US012577627B2

(12) United States Patent
Hecht et al.

(10) Patent No.: US 12,577,627 B2
(45) Date of Patent: Mar. 17, 2026

(54) SELECTIVE DETECTION OF DIFFERENT DENGUE VIRUS RNA SEROTYPES USING TANDEM TOEHOLD-MEDIATED DISPLACEMENT REACTIONS

(71) Applicants: ARIZONA BOARD OF REGENTS ON BEHALF OF ARIZONA STATE UNIVERSITY, Scottsdale, AZ (US); EMORY UNIVERSITY, Atlanta, GA (US)

(72) Inventors: Sidney Hecht, Phoenix, AZ (US); Jesse Waggoner, Atlanta, GA (US); Mingxuan Gao, Chongqing (CN); Shengxi Chen, Chandler, AZ (US)

(73) Assignees: ARIZONA BOARD OF REGENTS ON BEHALF OF ARIZONE STATE UNIVERSITY, Scottsdale, AZ (US); EMORY UNIVERSITY, Atlanta, GA (US)

( * ) Notice: Subject to any disclaimer, the term of this patent is extended or adjusted under 35 U.S.C. 154(b) by 1139 days.

(21) Appl. No.: 17/616,341

(22) PCT Filed: Jun. 3, 2020

(86) PCT No.: PCT/US2020/035852
§ 371 (c)(1),
(2) Date: Dec. 3, 2021

(87) PCT Pub. No.: WO2020/247448
PCT Pub. Date: Dec. 10, 2020

(65) Prior Publication Data
US 2022/0333216 A1    Oct. 20, 2022

Related U.S. Application Data

(60) Provisional application No. 62/856,284, filed on Jun. 3, 2019.

(51) Int. Cl.
*C12Q 1/6818* (2018.01)
*C12Q 1/70* (2006.01)

(52) U.S. Cl.
CPC ........... *C12Q 1/701* (2013.01); *C12Q 1/6818* (2013.01)

(58) Field of Classification Search
CPC ........ C12Q 1/70; C12Q 1/6818; C12Q 1/701; C12Q 2565/101
See application file for complete search history.

(56) References Cited

U.S. PATENT DOCUMENTS 4,469,863 A    9/1984   Ts'o et al.
5,034,506 A    7/1991   Summerton et al.
(Continued)

FOREIGN PATENT DOCUMENTS

WO    WO 2017/216270    12/2017

OTHER PUBLICATIONS

Gao et al., "Rapid detection of a dengue virus RNA sequence with single molecule sensitivity using tandem toehold-mediated displacement reactions," Chem. Commun., Jan. 2, vol. 54, pp. 968-971. (Year: 2018).*

(Continued)

*Primary Examiner* — Young J Kim
(74) *Attorney, Agent, or Firm* — Casimir Jones, S.C.; Anne M. Reynolds

(57) ABSTRACT
Described herein are systems and methods that may be used to differentially detect viral serotype specific nucleic acid. For example, these systems may comprise multiple DNA-nanostructures, capture oligonucleotides and protector oligonucleotides, wherein each DNA-nanostructure and its associated capture oligonucleotide and protector oligonucleotide are specific for a unique viral type or serotype.

11 Claims, 13 Drawing Sheets

Specification includes a Sequence Listing.

(56) References Cited

U.S. PATENT DOCUMENTS

| | | | |
|---|---|---|---|
| 5,216,141 | A | 6/1993 | Benner |
| 5,235,033 | A | 8/1993 | Summerton et al. |
| 5,386,023 | A | 1/1995 | Sanghvi et al. |
| 5,578,718 | A | 11/1996 | Cook et al. |
| 5,602,240 | A | 2/1997 | De Mesmaeker et al. |
| 5,637,684 | A | 6/1997 | Cook et al. |
| 5,644,048 | A | 7/1997 | Yau |
| 5,939,254 | A | 8/1999 | Ennis et al. |
| 6,773,885 | B1 | 8/2004 | Walder et al. |
| 7,439,341 | B2 | 10/2008 | Laikhter et al. |
| 2009/0227774 | A1 | 9/2009 | Turberfield et al. |
| 2017/0275711 | A1 | 9/2017 | Munoz-Jordan et al. |
| 2018/0371526 | A1 | 12/2018 | Chen et al. |

OTHER PUBLICATIONS

Tezuka et al., "Development of a novel dengue virus serotype-specific multiplex real-time reverse transcription-polymerase chain reaction assay for blood screening," Transfusion, December, vol. 56, pp. 3094-3100. (Year: 2016).*
International Search Report and Written Opinion for PCT/US2020/035852. Mailed Oct. 1, 2020. 11 pages.
Agrawal. Methods in Molecular Biology, vol. 26. Humana Press, Totowa, N.J., 1994. TOC only. 12 pages.
Beaucage et al., Deoxynucleoside phosphoramidites—A new class of key intermediates for deoxypolynucleotide synthesis. Tet. Let. 1981, 22(20), 1859-1862.
Beaucage et al., The Functionalization of Oligonucleotides Via Phosphoramidite Derivatives. Tetrahedron. 1993, 49(10), 1925-1963.
Borsenberger et al., Diene-modified nucleotides for the Diels-Alder-mediated functional tagging of DNA. Nucleic Acids Res. Apr. 2009;37(5):1477-85.
Brill et al., Synthesis of oligodeoxynucleoside phosphorodithioates via thioamidites. J. Am. Chem. Soc. 1989, 111, 6, 2321-2322.
Carlsson et al., Screening for genetic mutations. Nature. Mar. 21, 1996;380(6571):207.
Dempcy et al., Synthesis of a thymidyl pentamer of deoxyribonucleic guanidine and binding studies with DNA homopolynucleotides. Proc Natl Acad Sci U S A. Jun. 20, 1995;92(13):6097-101.
Douglas et al., Self-assembly of DNA into nanoscale three-dimensional shape. Nature. May 21, 2009; 459(7245): 414-418.
Duyen et al., Kinetics of plasma viremia and soluble nonstructural protein 1 concentrations in dengue: differential effects according to serotype and immune status. J Infect Dis. May 1, 2011;203(9):1292-300.
Eckstein. Oligonucleotides and Analogues: A Practical Approach, Oxford University Press. 1991. TOC only. 11 pages.
Egholm et al., Peptide nucleic acids (PNA). Oligonucleotide analogs with an achiral peptide backbone. J. Am. Chem. Soc. 1992, 114, 5, 1895-1897.
Egholm et al., PNA hybridizes to complementary oligonucleotides obeying the Watson-Crick hydrogen-bonding rules. Nature. Oct. 7, 1993;365(6446):566-8.
El-Sagheer et al., Click nucleic acid ligation: applications in biology and nanotechnology. Acc Chem Res. Aug. 21, 2012;45(8):1258-67.
Froehler et al., Synthesis of DNA via deoxynucleoside H-phosphonate intermediates. Nucleic Acids Res. Jul. 11, 1986;14(13):5399-407.
Gaffney et al., Large-scale oligonucleotide synthesis by the H-phosphonate method. Tet. Let. 1988, 29(22), 2619-2622.
Gao et al., Rapid detection of a dengue virus RNA sequence with single molecule sensitivity using tandem toehold-mediated displacement reactions. Chem Commun (Camb). Jan. 23, 2018;54(8):968-971.
Gao et al., Unusual conformation of a 3'-thioformacetal linkage in a DNA duplex. J Biomol NMR. Jan. 1994;4(1):17-34.
Garegg et al., Nucleoside H-phosphonates. III. Chemical synthesis of oligodeoxyribonucleotides by the hydrogenphosphonate approach. Tet. Let. 1986, 27(34):4051-4054.

Garegg et al., Nucleoside H-phosphonates. IV. Automated solid phase synthesis of oligoribonucleotides by the hydrogenphosphonate approach. Tet. Let. 1986, 27(34) :4055-4058.
He et al., Hierarchical self-assembly of DNA into symmetric supramolecular polyhedra. Nature. Mar. 13, 2008;452(7184):198-201.
Horn et al., Oligonucleotides with alternating anionic and cationic phosphoramidate linkages: Synthesis and hybridization of stereo-uniform isomers. Tetrahedron Lett. 1996, 37(6):743-746.
Jenkins et al., The Biosynthesis of Carbocyclic Nucleosides. Chem. Soc. Rev. 1995, 24(3), 169-176.
Jung et al., Hybridization of Alternating Cationic/Anionic Oligonucleotides to RNA Segments. Nucleosides and Nucleotides. 1994, 13(6-7), 1597-1605.
Letsinger et al., Cationic oligonucleotides. J. Am. Chem. Soc. 1988, 110, 13, 4470-4471.
Letsinger et al., Effects of pendant groups at phosphorus on binding properties of d-ApA analogues. Nucleic Acids Res. Apr. 25, 1986;14(8):3487-99.
Letsinger et al., Phosphoramidate analogs of oligonucleotides. J Org Chem. Nov. 1970;35(11):3800-3.
Mag et al., Synthesis and selective cleavage of an oligodeoxynucleotide containing a bridged internucleotide 5'-phosphorothioate linkage. Nucleic Acids Res. Apr. 11, 1991;19(7):1437-41.
Mbua et al., Strain-Promoted Alkyne-Azide Cycloadditions (SPAAC) Reveal New Features of Glycoconjugate Biosynthesis. Chembiochem, 2011, 12(12): 1912-1921.
Meier et al., Peptide Nucleic Acids(PNAs)—Unusual Properties of Nonionic Oligonucleotide Analogues. Chem. Int. Ed. Engl. 1992, 31(8): 1008-1010.
Mesmaeker et al., Comparison of rigid and flexible backbones in antisense oligonucleotides. Bioorganic & Medicinal Chem. Lett. 1994, 4(3): 395-398.
Rawls. Optimistic About Antisense Promising clinical results and chemical strategies for further improvements delight antisense drug researchers. Chem. Eng. News 1997, 75, 22, 35-39.
Rothemund. Folding DNA to create nanoscale shapes and patterns. Nature. Mar. 16, 2006;440(7082):297-302.
Sawai et al., Synthesis and Properties of Oligoadenylic Acids Containing 2'-5' Phosphoramide Linkage.Chem. Lett. 1984, 805-808.
Seeman. Nanomaterials based on DNA. Annu Rev Biochem. 2010;79:65-87.
Seo et al., Click chemistry to construct fluorescent oligonucleotides for DNA sequencing. J Org Chem. Jan. 24, 2003;68(2):609-12.
Sprinzl et al., Enzymatic incorporation of ATP and CTP analogues into the 3' end of tRNA. Eur J Biochem. Dec. 1977;81(3):579-89.
Tricou et al., Kinetics of viremia and NS1 antigenemia are shaped by immune status and virus serotype in adults with dengue. PLoS Negl Trop Dis. Sep. 2011;5(9):e1309. 1-10.
Von Kiedrowski et al., Parabolic Growth of a Self-Replicating Hexadeoxynucleotide Bearing a 3'-5'-Phosphoamidate Linkage. Angew. Chem. Int. Ed. Engl. 1991, 30(4), 423-426.
Waggoner et al., Characterization of Dengue Virus Infections Among Febrile Children Clinically Diagnosed With a Non-Dengue Illness, Managua, Nicaragua. J Infect Dis. Jun. 15, 2017;215(12):1816-1823.
Waggoner et al., Comparison of the FDA-approved CDC DENV-1-4 real-time reverse transcription-PCR with a laboratory-developed assay for dengue virus detection and serotyping. J Clin Microbiol. Oct. 2013;51(10):3418-20.
Waggoner et al., Single-reaction, multiplex, real-time rt-PCR for the detection, quantitation, and serotyping of dengue viruses. PLoS Negl Trop Dis. Apr. 18, 2013;7(4):e2116. 1-9.
Waggoner et al., Viremia and Clinical Presentation in Nicaraguan Patients Infected With Zika Virus, Chikungunya Virus, and Dengue Virus. Clin Infect Dis. Dec. 15, 2016;63(12):1584-1590.
Wei et al., Complex shapes self-assembled from single-stranded DNA tiles. Nature. May 30, 2012;485(7400):623-6.
Yurke et al., A DNA-fuelled molecular machine made of DNA. Nature. Aug. 10, 2000;406(6796):605-8.

(56)          References Cited

OTHER PUBLICATIONS

Zhang et al., DNA-affibody nanoparticles for inhibiting breast cancer cells overexpressing HER2. Chem Commun. 2017; 53(3):573-576.

Zhang et al., Dynamic DNA nanotechnology using strand-displacement reactions. Nat Chem. Feb. 2011;3(2):103-13.

Zhang et al., Engineering entropy-driven reactions and networks catalyzed by DNA. Science. Nov. 16, 2007;318(5853):1121-5.

Zhang et al., Exterior modification of a DNA tetrahedron. Chem Commun (Camb). Sep. 28, 2010;46(36):6792-4.

Zou et al., Polydopamine-embedded Cu2-xSe nanoparticles as sensitive biosensing platform through the coupling of nanometal surface energy transfer and photo-induced electron transfer. Analyst. 2015, 140:4121-4129.

* cited by examiner

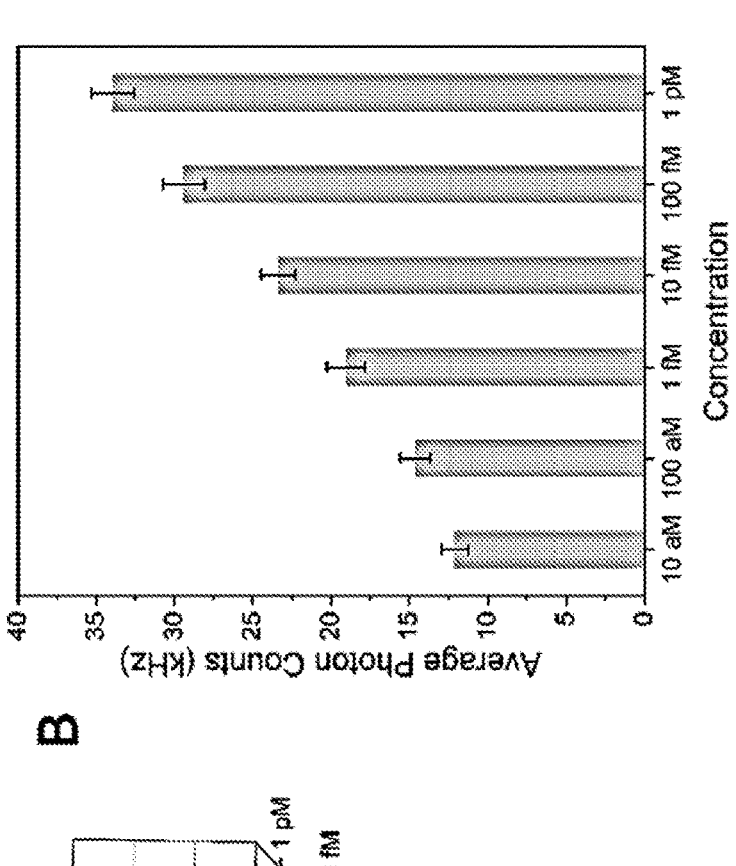
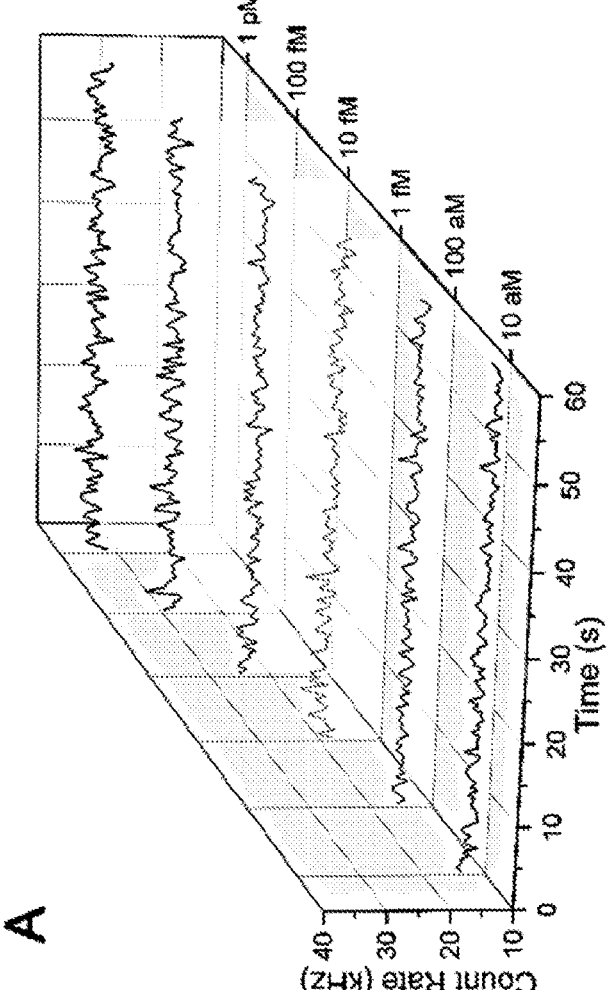
Fig. 5A – 5B

SELECTIVE DETECTION OF DIFFERENT DENGUE VIRUS RNA SEROTYPES USING TANDEM TOEHOLD-MEDIATED DISPLACEMENT REACTIONS

CROSS REFERENCE TO RELATED APPLICATIONS

This application is a U.S. national stage filing under 35 U.S.C. § 371 of International Patent Application No. PCT/ US2020/035852, filed on Jun. 3, 2020, which claims priority to U.S. Provisional Application No. 62/856,284, filed Jun. 3, 2019 which is hereby incorporated by reference herein in its entirety.

STATEMENT OF GOVERNMENT SUPPORT

This invention was made with government support under W81XWH-16-1-0141 awarded by ARMY/MRMC. The government has certain rights in the invention.

BACKGROUND

Dengue is the most widespread human arboviral disease and occurs primarily in tropical and subtropical regions of the world. Dengue results from infection with one of four related dengue viruses (DENV-1-4), which are mosquito borne flaviviruses transmitted by Aedes aegypti and Aedes albopictus. During the past 50 years, the global incidence of dengue has increased 30 fold. Currently, this disease threatens more than 2.5 billion people in more than 100 countries including the Americas, the Western Pacific, Southeast Asia, the Eastern Mediterranean, and Africa. It is estimated that 50-100 million symptomatic DENV infections occur annually, causing ~24,000 deaths.

The clinical symptoms that result from a DENV infection cannot be reliably differentiated from other causes of an acute febrile illness in regions of endemicity. As such, patients may receive inappropriate or delayed medical management, which can lead to poor outcomes. Early detection, facilitated through accurate and rapid diagnosis, is expected to inform care decisions and improve clinical outcomes. Dengue virus is a single-stranded, encapsulated positive-sense RNA virus with a genome of ~10.7 kb in length. There are four related DENV serotypes (DENV-1-4), of which DENV-2 and DENV-3 more frequently cause severe disease. As certain serotypes have different potential to cause severe disease, serotype-specific detection in the acute setting may help risk-stratify patients and target management for DENV.

During the acute phase, dengue virus can be isolated from patients to diagnose the infection and the serotypes. However, this technique requires cell culture, which is laborious and may require 1-2 weeks for confirmation. Serological and antigen-based diagnostics are available, including rapid, immunochromatographic tests for the DENV nonstructural protein 1 (NS1) antigen and anti-DENV IgM/IgG. The sensitivity of NS1 detection varies markedly, and in a representative study from Cambodia, assay sensitivity was 58% and specificity was 85%. To date, the diagnosis of dengue in the acute phase using reverse transcriptase-PCR (RT-PCR) to detect DENV RNA in whole blood, serum or plasma has been proven to be the most accurate diagnostic method. Real-time RT-PCR is now the most common technique. However, the design of rRT-PCRs requires a relatively large conserved region of the genome (60-80 bp) to include primers a hydrolysis probe. In addition, such methods require the use of expensive real-time instruments and labile reagents that necessitate reliable cold-storage. These factors limit capacity for molecular testing in many laboratory environments.

The toehold-mediated displacement reaction (TMDR) is a non-enzymatic kinetic-controlled process. In this process, a single-stranded toehold site, which neighbors a double strand helix, mediates strand displacement with another longer single-stranded oligonucleotide. Displacement occurs spontaneously at room temperature without requirement for enzymes. Previously, a tandem TMDR (tTMDR) method that was built into a rigid DNA tetrahedron to detect a conserved DENV RNA sequence. However, potential clinical applications of this technology have been limited by issues such as reaction leaks and high limits of detection, as the target nucleic acid is typically bound during the reaction. Further a study evaluating a TMDR for DENV detection was only evaluated with DNA and did not achieve a clinically-relevant limit of detection.

Accordingly, there is a need for improved methods that permit rapid, sensitive, and accurate diagnosis of viral disease, which can further distinguish between closely related viral serotypes. The present invention fulfills this need.

SUMMARY

In one embodiment, this disclosure relates to a system for detecting a nucleic acid from a virus or viral subtype in a sample, the composition comprising a) at least four DNA-nanostructures, wherein each of the at least four DNA-nanostructures comprises a hybridization region specific for a nucleic acid molecule from a unique viral type or viral serotype selected from the group consisting of DENV1, DENV2, DENV3, and DENV4, b) at least four associated protector oligonucleotides, wherein each of the at least four protector oligonucleotides is specific for hybridization to a unique DNA-nanostructure, and c) at least four associated capture oligonucleotides, wherein each of the at least four capture oligonucleotides is specific for hybridization to a unique DNA-nanostructure, wherein each of the at least four DNA-nanostructures is operably linked to one of a fluorophore or a quencher selected from a fluorophore quencher pair, wherein the quencher is capable of quenching the fluorescent light emitted from the fluorophore, and further wherein the associated protector oligonucleotide is operably linked to the other of a fluorophore and a quencher selected from the fluorophore quencher pair, wherein the viral nucleic acid is capable of displacing the associated protector oligonucleotide and hybridizing to the DNA-nanostructure; and wherein the associated capture oligonucleotide is capable of displacing the viral nucleic acid and hybridizing to the DNA-nanostructure but is not capable of displacing the associated protector oligonucleotide.

In one embodiment, the system comprises a DNA-nanostructure specific for DENV1, wherein the DNA-nanostructure is generated from hybridization of four oligonucleotides having at least about 95% sequence identity to SEQ ID NO:1, SEQ ID NO:5, SEQ ID NO:6 and SEQ ID NO:7.

In one embodiment, the system comprises a DNA-nanostructure specific for DENV2, wherein the DNA-nanostructure is generated from hybridization of four oligonucleotides having at least about 95% sequence identity to SEQ ID NO:2, SEQ ID NO:5, SEQ ID NO:6 and SEQ ID NO:7.

In one embodiment, the system comprises a DNA-nanostructure specific for DENV3, wherein the DNA-nanostructure is generated from hybridization of four oligonucleotides having at least about 95% sequence identity to SEQ ID NO:3, SEQ ID NO:5, SEQ ID NO:6 and SEQ ID NO:7.

In one embodiment, the system comprises a DNA-nanostructure specific for DENV4, wherein the DNA-nanostructure is generated from hybridization of four oligonucleotides having at least about 95% sequence identity to SEQ ID NO:4, SEQ ID NO:5, SEQ ID NO:6 and SEQ ID NO:7.

In one embodiment, the associated protector oligonucleotides comprise nucleic acid sequences having at least about 95% sequence identity to SEQ ID NO:8, SEQ ID NO:9, SEQ ID NO:10 and SEQ ID NO:11.

In one embodiment, the associated capture oligonucleotides comprise nucleic acid sequences having at least about 95% sequence identity to SEQ ID NO:12, SEQ ID NO:13, SEQ ID NO:14 and SEQ ID NO:15.

In one embodiment, the system comprises a single composition comprising four DNA-nanostructures, wherein each of the at least four DNA-nanostructures or each of the at least four associated protector oligonucleotides are operably linked to unique fluorescent molecules.

In one embodiment, each of the at least four DNA nanostructure and associated protector oligonucleotides are operably linked to a fluorophore quencher pair selected from the group consisting of TET/BHQ1, FAM/BHQ1, Quasar 570/BHQ2, TAMRA/BHQ2, JOE/BHQ1, ROX/BHQ2, Biosearch Blue/BHQ1, HEX/BHQ1, NED/BHQ2; Cy3/BHQ2, Cy5/BHQ2, Cy5/BHQ3 6-FAM/BHQ1, Yakima Yellow/BHQ1, TEX 615/BHQ2, Alexa Fluor® 488/BHQ1, VIC®/BHQ1, PET™/BHQ2, and Alexa Fluor® 594/BHQ2.

In one embodiment, this disclosure relates to a method of diagnosing a subject in need thereof as having an infection with a virus or viral serotype, the method comprising: a) obtaining a sample from the subject; b) contacting the sample from the subject with at least four DNA-nanostructures, wherein each DNA-nanostructure comprises a hybridization region specific for a unique viral type or viral serotype selected from the group consisting of DENV1, DENV2, DENV3, and DENV4, and further wherein each DNA-nanostructure is bound to an associated protector oligonucleotide; wherein each of the at least four DNA-nanostructures is operably linked to one of a fluorophore or a quencher selected from a fluorophore quencher pair, wherein the quencher is capable of quenching the fluorescent light emitted from the fluorophore, and further wherein the associated protector oligonucleotide specific for hybridizing to the DNA-nanostructure is operably linked to the other of the fluorophore and a quencher selected from the fluorophore quencher pair; and wherein the viral nucleic acid is capable of displacing the protector oligonucleotide and hybridizing to the DNA-nanostructure; c) contacting the reaction of step b) with at least four associated capture oligonucleotides, wherein each capture oligonucleotide is specific for hybridizing to one of the DNA-nanostructure and wherein the capture oligonucleotide is capable of displacing the viral nucleic acid and hybridizing to the DNA-nanostructure but is not capable of displacing the protector oligonucleotide, d) measuring fluorescence from the displaced protector oligonucleotide; and e) differentially diagnosing the subject as having a specific viral or viral serotype infection based on detection of fluorescence from a displaced protector oligonucleotide.

In one embodiment, the method comprises a DNA-nanostructure specific for DENV1, wherein the DNA-nanostructure is generated from hybridization of four oligonucleotides having at least about 95% sequence identity to SEQ ID NO:1, SEQ ID NO:5, SEQ ID NO:6 and SEQ ID NO:7.

In one embodiment, the method comprises a DNA-nanostructure specific for DENV2, wherein the DNA-nanostructure is generated from hybridization of four oligonucleotides having at least about 95% sequence identity to SEQ ID NO:2, SEQ ID NO:5, SEQ ID NO:6 and SEQ ID NO:7.

In one embodiment, the method comprises a DNA-nanostructure specific for DENV3, wherein the DNA-nanostructure is generated from hybridization of four oligonucleotides having at least about 95% sequence identity to SEQ ID NO:3, SEQ ID NO:5, SEQ ID NO:6 and SEQ ID NO:7.

In one embodiment, the method comprises a DNA-nanostructure specific for DENV4, wherein the DNA-nanostructure is generated from hybridization of four oligonucleotides having at least about 95% sequence identity to SEQ ID NO:4, SEQ ID NO:5, SEQ ID NO:6 and SEQ ID NO:7.

In one embodiment, the associated protector oligonucleotides comprise nucleic acid sequences having at least about 95% sequence identity to SEQ ID NO:8, SEQ ID NO:9, SEQ ID NO:10 and SEQ ID NO:11.

In one embodiment, the associated capture oligonucleotides comprise nucleic acid sequences having at least about 95% sequence identity to SEQ ID NO:12, SEQ ID NO:13, SEQ ID NO:14 and SEQ ID NO:15.

In one embodiment, the sample is aliquoted into at least four aliquots and contacted with each of the at least four DNA-nanostructures in parallel.

In one embodiment, this disclosure relates to a kit comprising a system for detecting a nucleic acid from a virus or viral subtype in a sample, the composition comprising a) at least four DNA-nanostructures, wherein each of the at least four DNA-nanostructures comprises a hybridization region specific for a nucleic acid molecule from a unique viral type or viral serotype selected from the group consisting of DENV1, DENV2, DENV3, and DENV4, b) at least four associated protector oligonucleotides, wherein each of the at least four protector oligonucleotides is specific for hybridization to a unique DNA-nanostructure, and c) at least four associated capture oligonucleotides, wherein each of the at least four capture oligonucleotides is specific for hybridization to a unique DNA-nanostructure, wherein each of the at least four DNA-nanostructures is operably linked to one of a fluorophore or a quencher selected from a fluorophore quencher pair, wherein the quencher is capable of quenching the fluorescent light emitted from the fluorophore, and further wherein the associated protector oligonucleotide is operably linked to the other of a fluorophore and a quencher selected from the fluorophore quencher pair, wherein the viral nucleic acid is capable of displacing the associated protector oligonucleotide and hybridizing to the DNA-nanostructure; and wherein the associated capture oligonucleotide is capable of displacing the viral nucleic acid and hybridizing to the DNA-nanostructure but is not capable of displacing the associated protector oligonucleotide.

In one embodiment, the kit of comprises: a) nucleic acid molecules for generation of a DNA-nanostructure specific for DENV1, wherein the DNA-nanostructure is generated from hybridization of four oligonucleotides having at least about 95% sequence identity to SEQ ID NO:1, SEQ ID NO:5, SEQ ID NO:6 and SEQ ID NO:7; b) nucleic acid molecules for generation of a DNA-nanostructure specific for DENV2, wherein the DNA-nanostructure is generated from hybridization of four oligonucleotides having at least about 95% sequence identity to SEQ ID NO:2, SEQ ID NO:5, SEQ ID NO:6 and SEQ ID NO:7; c) nucleic acid molecules for generation of a DNA-nanostructure specific for DENV3, wherein the DNA-nanostructure is generated from hybridization of four oligonucleotides having at least about 95% sequence identity to SEQ ID NO:3, SEQ ID NO:5, SEQ ID NO:6 and SEQ ID NO:7; d) nucleic acid molecules for generation of a DNA-nanostructure specific for DENV4, wherein the DNA-nanostructure is generated from hybridization of four oligonucleotides having at least about 95% sequence identity to SEQ ID NO:4, SEQ ID NO:5, SEQ ID NO:6 and SEQ ID NO:7; e) associated protector oligonucleotides comprising nucleic acid sequences having at least about 95% sequence identity to SEQ ID NO:8, SEQ ID NO:9, SEQ ID NO:10 and SEQ ID NO:11; and f) associated capture oligonucleotides comprising nucleic acid sequences having at least about 95% sequence identity to SEQ ID NO:12, SEQ ID NO:13, SEQ ID NO:14 and SEQ ID NO:15.

BRIEF DESCRIPTION OF THE DRAWINGS

The following detailed description of several embodiments of the disclosure will be better understood when read in conjunction with the appended drawings. It should be understood, however, that the disclosure is not limited to the precise arrangements and instrumentalities of the embodiments shown in the drawings.

FIG. 2A depicts an exemplary AFM image of the DNA tetrahedron for type 1 DENV RNA. FIG. 2B depicts an exemplary native polyacrylamide gel electrophoresis (PAGE) of the DNA tetrahedrons for four different serotypes of DENV RNA. Lane M represents the DNA marker, lane 1 to 4 represent the DNA tetrahedrons for detecting type 1 to 4 DENV RNA respectively.

FIG. 3A depicts an exemplary fluorescence spectra of four DNA tetrahedrons with/without BHQ-1. FIG. 3B depicts an exemplary fluorescence spectra of four quenched DNA tetrahedrons in the presence of four synthetic RNAs.

FIG. 4A depicts an exemplary fluorescence image of in the presence of different concentrations of synthetic RNAs (left to right): 0, 0.01, 0.1, 0.5, 1.0, 10 nM. FIG. 4B depicts an exemplary histogram of fluorescent spectra intensities of the corresponding spots.

FIG. 5A depicts an exemplary photon count rate of the DENV-1 tetrahedron in the presence of different concentration of DENV-1 synthetic dengue viral RNA.

FIG. 5B depicts an exemplary histogram of average photon counts of serotype 1 tetrahedron in the presence of different concentration of DENV-1 synthetic DENV RNA in 60 seconds.

FIG. 9A depicts exemplary fluorescent images for specificity assay between different serotypes of DENV RNA. FIG. 9B depicts exemplary fluorescent images for exclusivity assay of DNA tetrahedrons reacting with negative control (NC) RNA, Zika virus and yellow fever virus genomic RNA. FIG. 9C depicts an exemplary histogram of fluorescent spectra intensities of the specificity assay results. FIG. 9D depicts an exemplary histogram of fluorescent spectra intensities of the exclusivity assay results.

FIG. 10A depicts an exemplary photon count rate of the DENV-1 RNA. Px: sample number; wb: whole blood; p: plasma. FIG. 10B depicts exemplary fluorescent images for the detection of different serotypes of DENV RNA from 8 patients.

DETAILED DESCRIPTION

Figure 1:
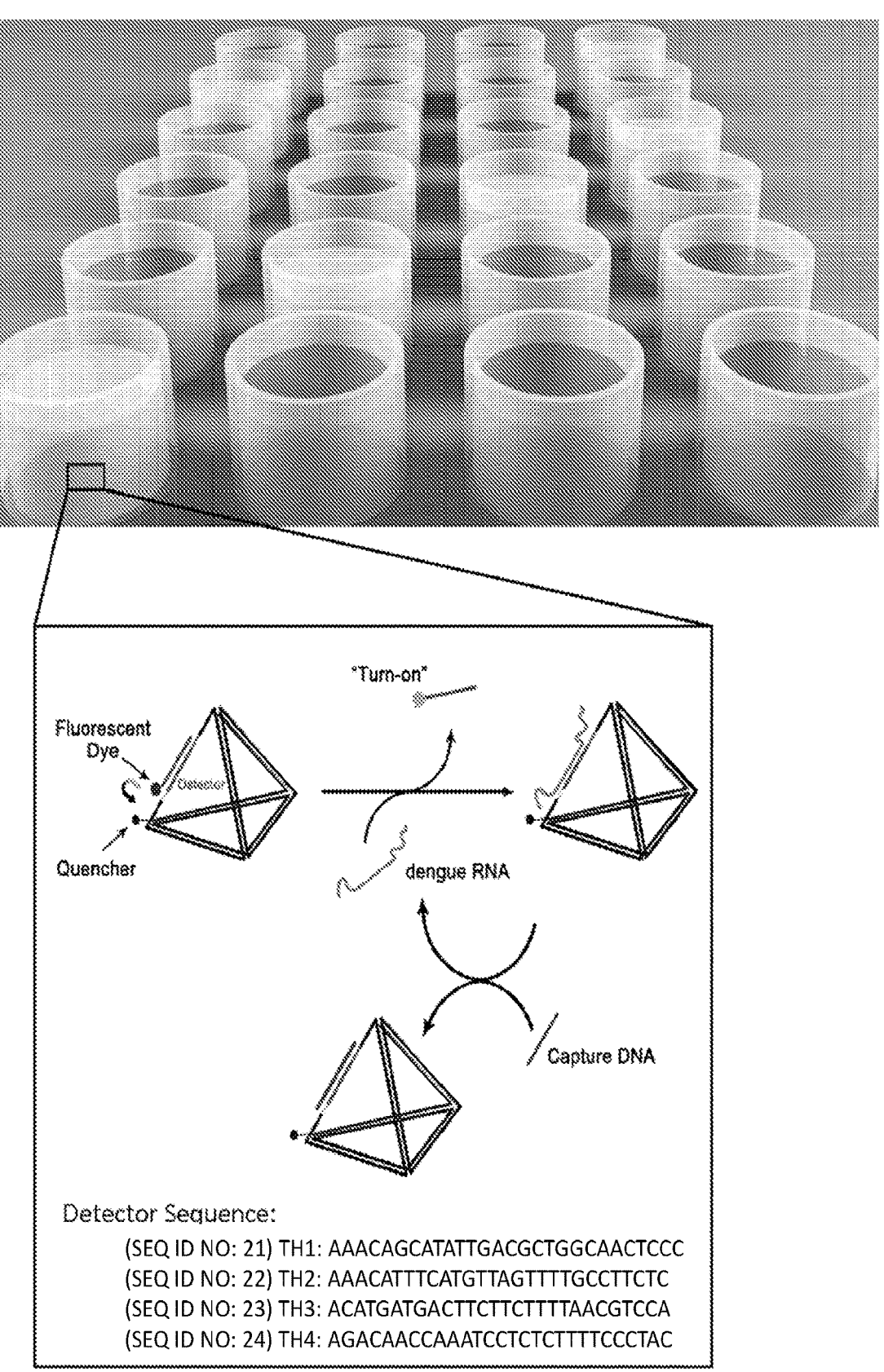
FIG. 1 depicts a diagram of the strategy to detect serotypes of DENV RNA using tTMDRs. Top panel, array on a 384-well plate for diagnosis of four serotypes of DENV RNA. Bottom panel, strategy to amplify a fluorescent signal on a DNA tetrahedron using tTMDRs.

In the systems and methods of the present disclosure, at least one, two, three or four unique DNA-nanostructures are used in parallel assays or as a single assay to detect a viral serotype. In one embodiment, the systems and assays of the present disclosure include a combination of four different DNA-nanostructures, with each DNA-nanostructure being specific for detection of a single Dengue viral serotype (e.g., one of DENV1, DENV2, DENV3 or DENV4), allowing for identification of the specific Dengue viral serotype present in the sample being tested.

As described herein, a duo-toehold-mediated strand displacement (TMDR) method in combination with FRET was developed to detect the presence of viral serotype specific nucleic acid in a sample (e.g., dengue RNA). Specifically, four different DNA-nanostructures were developed, with each designed to specifically amplify the detection signal of a single dengue viral serotype nucleic acid. In the TMDR process, a target nucleic acid anneals to a complementary DNA sequence via a first toehold in the DNA-nanostructure, displaces a protector DNA and recovers the fluorescence from a quenched fluorophore. Then, a capture DNA displaces the target nucleic acid via a second toehold in the DNA-nanostructure. The target nucleic acid can then be recycled in the first TMDR process and form an amplifying loop, thereby enhancing the fluorescence signal.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present disclosure, some exemplary methods and materials are described.

"About" as used herein when referring to a measurable value such as an amount, a temporal duration, and the like, is meant to encompass variations of ±20% or ±10%, ±5%, ±1%, or ±0.1% from the specified value, as such variations are appropriate to perform the disclosed methods.

The singular forms "a," "and" and "the" include plural references unless the context clearly dictates otherwise. The present disclosure also contemplates other embodiments "comprising," "consisting of" and "consisting essentially of" the embodiments or elements presented herein, whether explicitly set forth or not.

As used herein, an "adaptor" of the present disclosure means a piece of nucleic acid that is added to a nucleic acid of interest, e.g., the polynucleotide. In one embodiment, two adaptors of the present disclosure are ligated to the ends of a DNA fragment cross-linked to a polypeptide of interest, with one adaptor on each end of the fragment. Adaptors of the present disclosure can comprise a primer binding sequence, a random nucleotide sequence, a barcode, or any combination thereof.

An affinity label, as the term us used herein, refers to a moiety that specifically binds another moiety and can be used to isolate or purify the affinity label, and compositions to which it is bound, from a complex mixture. One example of such an affinity label is a member of a specific binding pair (e.g, biotin:avidin, antibody:antigen). The use of affinity labels such as digoxigenin, dinitrophenol or fluorescein, as well as antigenic peptide 'tags' such as polyhistidine, FLAG, HA and Myc tags, is envisioned.

"Amplification," as used herein, refers to any in vitro process for increasing the number of copies of a nucleotide sequence or sequences, i.e., creating an amplification product which may include, by way of example additional target molecules, or target-like molecules or molecules complementary to the target molecule, which molecules are created by virtue of the presence of the target molecule in the sample. These amplification processes include but are not limited to polymerase chain reaction (PCR), multiplex PCR, Rolling Circle PCR, ligase chain reaction (LCR) and the like, in a situation where the target is a nucleic acid, an amplification product can be made enzymatically with DNA or RNA polymerases or transcriptases. Nucleic acid amplification results in the incorporation of nucleotides into DNA or RNA. As used herein, one amplification reaction may consist of many rounds of DNA replication. PCR is an example of a suitable method for DNA amplification. For example, one PCR reaction may consist of 2-40 "cycles" of denaturation and replication.

"Amplification products," "amplified products" "PCR products" or "amplicons" comprise copies of the target sequence and are generated by hybridization and extension of an amplification primer. This term refers to both single stranded and double stranded amplification primer extension products which contain a copy of the original target sequence, including intermediates of the amplification reaction.

"Appropriate hybridization conditions" as used herein may mean conditions under which a first nucleic acid sequence (e.g., primer, etc.) will hybridize to a second nucleic acid sequence (e.g., target, etc.), such as, for example, in a complex mixture of nucleic acids. Appropriate hybridization conditions are sequence-dependent and will be different in different circumstances. In one embodiment, appropriate hybridization conditions may be selective or specific wherein a condition is selected to be about 5-10° C. lower than the thermal melting point ($T_m$) for the specific sequence at a defined ionic strength and pH. In one embodiment, an appropriate hybridization condition encompasses hybridization that occurs over a range of temperatures from more to less stringent. In one embodiment, a hybridization range may encompass hybridization that occurs from 98° C. to 50° C. According to the disclosure, such a hybridization range may be used to allow hybridization of the primers of the disclosure to target sequences with reduced specificity, for the purposes of amplifying a broad range of nucleic acid molecules with a single set of primers.

As used herein, "binding" means an association interaction between two molecules, via covalent or non-covalent interactions including, but not limited to, hydrogen bonding, hydrophobic interactions, van der Waals interactions, and electrostatic interactions. Binding may be sequence specific or non-sequence specific. Non-sequence specific binding may occur when, for example, a polypeptide of interest (i.e. a histone) binds to a polynucleotide of any sequence. Specific binding may occur when, for example, a polypeptide of interest (i.e. a transcription factor) binds predominantly to a highly restricted sequence of nucleotides.

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

As used herein, the term "derived" or "directed to" with respect to a nucleotide molecule means that the molecule has complementary sequence identity to a particular molecule of interest.

As used herein, "dNTPs" refers to a mixture of different deoxyribonucleotide triphosphates: deoxyadenosine triphosphate (dATP), deoxycytidine triphosphate (dCTP), deoxyguanosine triphosphate (dGTP) and deoxythymidine triphosphate (dTTP).

"Fragment" as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between).

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. When comparing DNA and RNA, thymine (T) and uracil (U) may be considered equivalent. Identity may be performed manually or by using a computer sequence algorithm such as BLAST or BLAST 2.0.

"Nucleic acid" or "oligonucleotide" or "polynucleotide" or "nucleic acid fragment" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence. Thus, a nucleic acid also encompasses a probe that hybridizes under appropriate hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine.

Modified nucleotides are known in the art and include, by example and not by way of limitation, alkylated purines and/or pyrimidines; acylated purines and/or pyrimidines; or other heterocycles. These classes of pyrimidines and purines are known in the art and include, pseudoisocytosine; N4, N4-ethanocytosine; 8-hydroxy-N6-methyladenine; 4-acetyl-cytosine, 5-(carboxyhydroxylmethyl) uracil; 5-fluorouracil; 5-bromouracil; 5-carboxymethylaminomethyl-2-thiouracil; 5-carboxymethylaminomethyl uracil; dihydrouracil; inosine; N6-isopentyl-adenine; 1-methyladenine; 1-methylpseudouracil; 1-methylguanine; 2,2-dimethylguanine; 2-methyladenine; 2-methylguanine; 3-methylcytosine; 5-methylcytosine; N6-methyladenine; 7-methylguanine; 5-methylaminomethyl uracil; 5-methoxy amino methyl-2-thiouracil; β-D-mannosylqueosine; 5-methoxycarbonylm-ethyluracil; 5-methoxyuracil; 2-methylthio-N6-isopentenyl-adenine; uracil-5-oxyacetic acid methyl ester; pseudouracil; 2-thiocytosine; 5-methyl-2 thiouracil, 2-thiouracil; 4-thiouracil; 5-methyluracil; N-uracil-5-oxyacetic acid methyl ester; uracil 5-oxyacetic acid; queosine; 2-thiocytosine; 5-propyluracil; 5-propylcytosine; 5-ethyluracil; 5-ethylcytosine; 5-butyluracil; 5-pentyluracil; 5-pentylcytosine; and 2,6,-diaminopurine; methylpseudouracil; 1-methylguanine; 1-methylcytosine. Backbone modifications are similarly known in the art, and include, chemical modifications to the phosphate linkage (e.g., phosphorodiamidate, phosphoroth-ioate (PS), N3' phosphoramidate (NP), boranophosphate, 2',5' phosphodiester, amide-linked, phosphonoacetate (PACE), morpholino, peptide nucleic acid (PNA) and inverted linkages (5'-5' and 3'-3' linkages)) and sugar modifications (e.g., 2'-O-Me, UNA, LNA).

A "mutation" or "variation" as used herein, refers to a change in nucleic acid or polypeptide sequence relative to a parental or reference sequence, and includes translocations, deletions, insertions, and substitutions/point mutations. A "mutant" or "variant" as used herein, refers to either a nucleic acid or protein comprising a mutation.

As used herein, the term "nanostructure" is defined to mean any structure having a distinct shape formed from a plurality of elements. For example, the shape may include linear forms, circular forms, two-dimensional patterns or three-dimensional structures. In one embodiment, at least one dimension of the structure is on the nanoscale, i.e. in the range between 0.1 and 100 nm. For example, two-dimensional patterns may have a thickness on the nanoscale. In one embodiment, nanotubes have two dimensions on the nanoscale, i.e. the diameter of the tube is between 0.1 and 100 nm while the length could be much greater.

The oligonucleotides described herein may be synthesized using standard solid or solution phase synthesis techniques which are known in the art. In certain embodiments, the oligonucleotides are synthesized using solid-phase phosphoramidite chemistry (U.S. Pat. No. 6,773,885) with automated synthesizers. Chemical synthesis of nucleic acids allows for the production of various forms of the nucleic acids with modified linkages, chimeric compositions, and nonstandard bases or modifying groups attached in chosen places through the nucleic acid's entire length.

Certain embodiments encompass isolated or substantially purified nucleic acid compositions. In the context of the present disclosure, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule is substantially free of other cellular material or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived.

"Operably-linked" refers to the association two chemical moieties so that the function of one is affected by the other, e.g., an arrangement of elements wherein the components so described are configured so as to perform their usual function.

"Primer" as used herein refers to a single-stranded oligonucleotide or a single-stranded polynucleotide that is extended on its 3' end by covalent addition of nucleotide monomers during amplification. Nucleic acid amplification often is based on nucleic acid synthesis by a nucleic acid polymerase. Many such polymerases require the presence of a primer that can be extended to initiate such nucleic acid synthesis.

As used herein, "purifying" the polynucleotides of the present disclosure refers to a process well known to those of skill in the art in which polynucleotides are substantially separated from other components in a sample, including, but not limited to, polypeptides of interest.

As used herein, "sample" or "test sample," may refer to any source used to obtain nucleic acids for examination using the compositions and methods of the disclosure. A test sample is typically anything suspected of containing a target sequence. Test samples can be prepared using methodologies well known in the art such as by obtaining a specimen from an individual and, if necessary, disrupting any cells contained thereby to release genomic nucleic acids. These test samples include biological samples which can be tested by the methods of the present disclosure described herein and include human and animal cells, tissues and body fluids such as whole blood, serum, plasma, cerebrospinal fluid, sputum, bronchial washing, bronchial aspirates, urine, lymph fluids and various external secretions of the respiratory, intestinal and genitourinary tracts, tears, saliva, milk, white blood cells, myelomas, buccal cells, cervicovaginal cells, epithelial cells from urine, fetal cells, or any cells present in tissue obtained by biopsy and the like; biological fluids such as cell culture supernatants; tissue specimens which may be fixed; and cell specimens which may be fixed.

Any nucleic acid sample may be used in practicing the present disclosure, including without limitation eukaryotic, prokaryotic and viral nucleic acid. In one embodiment, the target nucleic acid represents a viral RNA in a sample isolated from a patient. The patient sample may be obtained from any cell source, tissue source, or body fluid. Body fluids include blood, urine, cerebrospinal fluid, semen and tissue exudates at the site of infection or inflammation.

"Substantially complementary" as used herein may mean that a first sequence is at least 95%, 96%, 97%, 98% or 99% identical to the complement of a second sequence over a region of about 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under appropriate hybridization conditions.

"Substantially identical" as used herein may mean that a first and second sequence are at least 95%, 96%, 97%, 98%, or 99% over a region of about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides or amino acids, or with respect to nucleic acids, if the first sequence is substantially complementary to the complement of the second sequence.

A "target nucleic acid" as the term is used herein, refers to a nucleic acid to which another nucleic acid binds in the context of the cellular environment. Typically such binding is through complementarity of the respective nucleic acid sequences.

The term "therapeutically effective amount," in reference to treating a disease state/condition, refers to an amount of a therapeutic agent that is capable of having any detectable, positive effect on any symptom, aspect, or characteristics of a disease state/condition when administered as a single dose or in multiple doses. Such effect need not be absolute to be beneficial.

The terms "treat" and "treatment" refer to both therapeutic treatment and prophylactic or preventative measures, wherein the object is to prevent or decrease an undesired physiological change or disorder. For purposes of this disclosure, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

Toehold-mediated displacement reaction (TMDR) is a kinetic-controlled non-enzymatic process. In this process, a single stranded oligonucleotide (referred to as a toehold), which is adjacent to a double strand duplex, mediates a displacement with another single stranded oligonucleotide. This process can occur spontaneously at room temperature without any other assistance.

As described herein, a novel duo-toehold-mediated strand displacement method in combination with FRET was developed to detect the presence of viral nucleic acid in a sample (e.g., dengue RNA). Specifically, a DNA-nanostructure was developed to amplify the detection signal of a viral nucleic acid. In the first TMDR process, a target nucleic acid anneals to a complementary DNA sequence via a first toehold in the DNA-nanostructure, displaces a protector DNA and recovers the fluorescence from a quenched fluorophore. In the second TMDR process, a capture DNA displaces the target nucleic acid via a second toehold in the DNA-nanostructure. The target nucleic acid can then be recycled in the first TMDR process and form an amplifying loop, thereby enhancing the fluorescence signal. As described in the Example, the limit of this detection method was as low as 10 pM, which was more sensitive by 3 orders of magnitude than traditional non-amplified detecting methods. Using a single molecule detecting technique, the limit of detection could be as low as 0.1 aM, which means only about six copies of target RNA presented in the sample. Accordingly, certain methods and compositions of the disclosure are provided below.

DNA-Nanostructures

DNA-nanostructures are nanoscale structures made of DNA, wherein the DNA acts both as a structural and function element. DNA-nanostructures can serve as a scaffold for the formation of other structures. DNA-nanostructures may be prepared by methods known in the art using nucleic acid oligonucleotides. For example, such nanostructures may be assembled based on the concept of base-pairing, and while in certain embodiments, no specific sequence is required, the sequences of each oligonucleotide are partially complementary to certain other oligonucleotides to enable hybridization of all strands.

A nucleic acid oligonucleotide of the present disclosure can be single-stranded or double stranded and will generally contain phosphodiester bonds, although in some cases, as outlined below, nucleic acid analogs are included that may have alternate backbones, comprising, for example, phosphoramide (Beaucage et al. (1993) Tetrahedron 49(10): 1925) and references therein; Letsinger (1970) J. Org. Chem. 35:3800; Sprinzl et al. (1977) Eur. J. Biochem. 81: 579; Letsinger et al. (1986) Nucl. Acids Res. 14: 3487; Sawai et al. (1984) Chem. Lett. 805, Letsinger et al. (1988) J. Am. Chem. Soc. 110: 4470; and Pauwels et al. (1986) Chemica Scripta 26: 1419), phosphorothioate (Mag et al. (1991) Nucleic Acids Res. 19:1437; and U.S. Pat. No. 5,644,048), phosphorodithioate (Briu et al. (1989) J. Am. Chem. Soc. 111:2321, O-methylphosphoroamidite linkages (see Eckstein, Oligonucleotides and Analogues: A Practical Approach, Oxford University Press), and peptide nucleic acid backbones and linkages (see Egholm (1992) J. Am. Chem. Soc. 114:1895; Meier et al. (1992) Chem. Int. Ed. Engl. 31: 1008; Nielsen (1993) Nature, 365: 566; Carlsson et al. (1996) Nature 380: 207). Other analog nucleic acids include those with positive backbones (Denpcy et al. (1995) Proc. Natl. Acad. Sci. USA 92: 6097; non-ionic backbones (U.S. Pat. Nos. 5,386,023, 5,637,684, 5,602,240, 5,216,141 and 4,469,863; Angew. (1991) Chem. Intl. Ed. English 30: 423; Letsinger et al. (1988) J. Am. Chem. Soc. 110:4470; Letsinger et al. (1994) Nucleoside & Nucleotide 13:1597; Chapters 2 and 3, ASC Symposium Series 580, "Carbohydrate Modifications in Antisense Research", Ed. Y. S. Sanghui and P. Dan Cook; Mesmaeker et al. (1994), Bioorganic & Medicinal Chem. Lett. 4: 395; Jeffs et al. (1994) J Biomolecular NMR 34:17; Tetrahedron Lett. 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghui and P. Dan Cook. Nucleic acids containing one or more carbocyclic sugars are also included within the definition of nucleic acids (see Jenkins et al. (1995), Chem. Soc. Rev. pp 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The length of each oligonucleotide or DNA strand is variable and depends on, for example, the type of nanostructure. In certain embodiments, the oligonucleotide or DNA strand is about 15 nucleotides in length to about 500 nucleotides in length, about 15 to about 200 nucleotides in length, or about 15 to about 100 nucleotides in length.

For use in the present disclosure, the nucleic acids can be synthesized de novo using any of a number of procedures well known in the art. Nucleic acids may be isolated from natural sources or purchased from commercial sources. In certain exemplary embodiments, nucleic acids or nucleic acid-binding molecules may be prepared using one or more of the phosphoramidite linkers and/or sequencing by ligation methods known to those of skill in the art. For example, the cyanoethyl phosphoramidite method (Beaucage, S. L., and Caruthers, M. H., Tet. Let. 22:1859, 1981); nucleoside H-phosphonate method (Garegg et al., Tet. Let. 27:4051-4054, 1986; Froehler et al., Nucl. Acid. Res. 14:5399-5407, 1986; Garegg et al., Tet. Let. 27:4055-4058, 1986, Gaffney et al., Tet. Let. 29:2619-2622, 1988), or by any other chemical method using either a commercial automated oligonucleotide synthesizer or high-throughput, high-density array methods known in the art. Pre-synthesized oligonucleotides may also be obtained commercially from a variety of vendors.

In certain exemplary embodiments, nucleic acids may be prepared using a variety of micro-array technologies known in the art. Pre-synthesized nucleic acids or nucleic acid-binding molecules may be attached to a support or synthesized in situ using light-directed methods, flow channel and spotting methods, ink-jet methods, pin-based methods and bead-based methods known in the art.

Nucleic acid origami structures, also referred to as DNA origami structures or DNA origami, are two- or three-dimensional arbitrary shapes formed from nucleic acids. The term "origami" infers that one or more strands or building blocks of DNA (called scaffold strands) may be folded or otherwise positioned into a desired structure or shape. The desired structure or shape which may then be secured into a desired shape or structure by one or more other strands or building blocks of DNA. Methods of DNA origami are described for example by Rothemund, 2006, Nature, 440: 297-302; Douglas et al., 2009, Nature, 459: 414-418; and Seeman, 2010, Biochem. 79:65-87, all of which are incorporated herein by reference in their entirety.

A nucleic acid origami structure for use in the systems and methods of the disclosure can be constructed using single-stranded nucleic acid sequences which self-assemble into tiles to form lattices of any desired shape or size. Such approaches include programmed self-assembly of designed strands of nucleic acids to create a wide range of structures with designed shapes (Wei et al., 2012, Nature, 485:623-627; herein incorporated by reference in its entirety).

A DNA nanostructure for use in the systems and methods of the disclosure may be of any arbitrary shape as desired, including, but not limited to a rectangular DNA origami nanostructure, a triangular DNA origami nanostructure, a tubular DNA origami nanostructure, a tetrahedral DNA origami nanostructure, a pentahedral DNA origami nanostructure, a hexahedral DNA origami nanostructure, a septahedral DNA origami nanostructure, an octahedral DNA origami nanostructure, a nonahedral DNA origami nanostructure, a decahedral DNA origami nanostructure, a hendecahedral DNA origami nanostructure, and a dodecahedral DNA origami nanostructure.

In one embodiment, the DNA origami nanostructure for use in the systems and methods of the disclosure is (i) structurally stable under ambient conditions, (ii) contains at least one single-stranded edge comprising a target hybridization domain for hybridization to a protector/target/capture nucleic acid and at least one toehold region, and (iii) wherein a hybridized, protector DNA can be displaced by the complementary target (e.g., viral) nucleic acid over a period ranging from a few minutes to several hours.

In some embodiments, the methods of the disclosure incorporate the use of TMDR nanostructures comprising at least one single stranded region, comprising two toehold domains flanking a target hybridization domain. In one embodiment, portions of the single stranded region are also complementary to the protector oligonucleotide, the viral nucleic acid and the capture oligonucleotide.

In certain embodiments, the first toehold domain may be used by the viral nucleic acid to displace the protector oligonucleotide and the second toehold domain may be used by the capture oligonucleotide to displace the viral nucleic acid. In one embodiment, the toehold domain comprises a nucleic acid sequence that is complementary to a region of the displacing strand (e.g., the viral nucleic acid or the capture oligonucleotide) and is located adjacent to a double stranded region comprising the strand to be displaced (e.g., the protector strand bound to the DNA-nanostructure or the viral nucleic acid bound to the DNA-nanostructure). In one embodiment, the toehold domain is long enough to enable sufficient hybridization for strand displacement to occur.

While the toehold domain may be longer or shorter, such a domain typically includes between about 4 to about 15 nucleotides, or about 5 to about 8 nucleotides.

Accordingly, in certain embodiments, the DNA-nano-structure comprises a single stranded nucleic acid sequence that comprises a first toehold domain, a hybridization region and a second toehold domain. In certain embodiments, the first toehold domain comprises a nucleic acid sequence that is complementary to a portion of the viral nucleic acid. In certain embodiments, the hybridization region comprises a nucleic acid sequence that is complementary to a portion of the viral nucleic acid, the protector oligonucleotide and the capture oligonucleotide. In certain embodiments, the second toehold domain comprises a nucleic acid sequence that is complementary to a portion of the protector oligonucleotide and a portion of the capture oligonucleotide. In certain embodiments, the viral nucleic acid does not hybridize to the second toehold domain. In certain embodiments, the pro-tector oligonucleotide does not hybridize to the first toehold domain. In certain embodiments, the first toehold domain is linked to the 5' end of the hybridization region and the second toehold domain is linked to the 3' end of the hybridization region (e.g., linked through a phosphodiester bond). In certain embodiments, the first toehold domain is linked to the 3' end of the hybridization region and the second toehold domain is linked to the 5' end of the hybridization region (e.g., linked through a phosphodiester bond).

In certain embodiments, the DNA-nanostructure com-prises a single stranded nucleic acid sequence comprising a first toehold domain; a hybridization region; and a second toehold domain; wherein, the hybridization region and the second toehold domain comprise nucleic acid sequences that are complementary to the protector oligonucleotide and the capture oligonucleotide; and wherein the first toehold domain and hybridization region comprise sequences that are complementary to the viral nucleic acid.

As described herein, the DNA-nanostructure is operably linked to a fluorophore/quencher. In one embodiment, the fluorophore/quencher is operably linked in proximity to the single stranded region of the DNA-nanostructure, such that quenching may occur between fluorophore/quencher linked to the DNA-nanostructure and the fluorophore/quencher operably linked to the protector oligonucleotide.

In certain embodiments, the quencher and fluorophore are separated by between about 1 to about 60 base pairs, about 1 to about 50 base pairs, about 1 to about 40 base pairs, about 1 to about 30 base pairs, about 1 to about 20 base pairs, about 1 to about 15 base pairs or about 1 to about 10 base pairs. In certain embodiments, the quencher and fluorophore are separated by between about 9, 8, 7, 6, 5, 4, 3, 2 or about 1 base pair(s).

In certain embodiments, a quencher is operably linked to the DNA-nanostructure and a fluorophore is operably linked to the protector oligonucleotide.

In certain embodiments, a fluorophore is operably linked to the DNA-nanostructure and a quencher is operably linked to the protector oligonucleotide.

In certain embodiments, the DNA-nanostructure is a DNA-tetrahedron. In certain embodiments, the DNA-tetra-hedrons may be prepared by methods described in Zhang, et al., Chem Commun, 46, 6792-6794 (2010) and He et al., Nature, 2008, 452, 198, which are herein incorporated by reference.

In certain embodiments, the DNA-tetrahedron comprises five double-stranded edges and 1 single stranded edge. In some embodiments, each double stranded edge comprises 20 base pairs, and the single stranded edge comprises 28 nucleotides.

In certain embodiments, a fluorophore or quencher is operably linked at the vertex of the tetrahedron proximal to the single stranded edge.

In certain embodiments, the DNA-nanostructure is formed from hybridization of four DNA oligonucleotides. In certain embodiments, the DNA nanostructure is a DNA-tetrahedron formed from hybridization of four DNA oligo-nucleotides, wherein three of the oligonucleotides comprise SEQ ID NO:5, SEQ ID NO:6 and SEQ ID NO:7, or variants thereof, and the fourth oligonucleotide comprises a first nanostructure-hybridization domain on the 5' end of the oligonucleotide and a second nanostructure-hybridization domain on the 3' end of the oligonucleotide, wherein the first and second nanostructure-hybridization domains promote the formation of the DNA-tetrahedron and wherein the fourth oligonucleotide further comprises a variable target hybridization region. In one embodiment, the fourth oligo-nucleotide comprises a sequence of TGCTCTTCCC-GANNNNNNNNNNNNNNNNNNNNNNNNNNNNNACT-CAACTGCCTG GTGATACGAGGATGGGCA (SEQ ID NO:20), or a variant thereof. In certain embodiments, the DNA tetrahedron is generated through hybridization of four DNA oligonucleotides comprising a nucleic acid sequences independently having at least about 95%, 96%, 97%, 98%, 99% or 100% sequence identity to SEQ ID NO:5, SEQ ID NO:6, SEQ ID NO:7 and SEQ ID NO:20. In certain embodi-ments, a fluorophore or quencher is operably linked to SEQ ID NO:7. In certain embodiments, a fluorophore or quencher is operably linked to the 5' end of SEQ ID NO:7. In certain embodiments, a fluorophore or quencher is operably linked to the 3' end of SEQ ID NO:7. In certain embodiments, a quencher (e.g., BHQ-1) is operably linked to the 5' end of SEQ ID NO:7.

In certain embodiments, the fourth oligonucleotide com-prises a target hybridization domain and two nucleotide sequences that can function as toehold domains, wherein the two toehold domains flank the target hybridization domain. In certain embodiments, the fourth oligonucleotide com-prises from 5' to 3' a first nanostructure hybridization domain, a first toehold domain, a target capture domain, a second toehold domain and a second nanostructure hybrid-ization domain, wherein the first toehold domain, the target hybridization domain and the second toehold domain form the ssDNA side of a DNA tetrahedron nanostructure after hybridization. In certain embodiments, the fourth oligo-nucleotide comprises a nucleic acid sequence of

AAACAGCATATTGACGCTGGCAACTCCC (SEQ ID NO:21),

AAACATTTCATGTTAGTTTTGCCTTCTC (SEQ ID NO:22),

ACATGATGACTTCTTCTTTTAACGTCCA (SEQ ID NO:23), or

AGACAACCAAATCCTCTCTTTTCCCTAC (SEQ ID NO:24), or a fragment or variant thereof. In certain embodiments, the fourth oligonucleotide comprises a nucleic acid sequence of SEQ ID NO:1, SEQ ID NO:2, SEQ ID NO:3 or SEQ ID NO:4, or a fragment or variant thereof. In certain embodiments, the fourth DNA oligonucleotide comprises a nucleic acid sequence having at least about 95%, 96%, 97%, 98%, 99% or 100% sequence identity to SEQ ID NO:1, SEQ ID NO:2, SEQ ID NO:3, SEQ ID NO:4, SEQ ID NO:21, SEQ ID NO:22, SEQ ID NO:23 or SEQ ID NO:24.

In certain embodiments, the DNA-tetrahedron is used to detect a dengue serotype 1 (DENV1) nucleic acid (e.g., RNA), and is formed from hybridization of four DNA oligonucleotides comprising at least about 75% sequence identity to SEQ ID NO:1, SEQ ID NO:5, SEQ ID NO:6 and SEQ ID NO:7. In certain embodiments, the four DNA oligonucleotides comprise nucleic acid sequences independently having at least about 95%, 96%, 97%, 98%, 99% or 100% sequence identity to SEQ ID NO:1, SEQ ID NO:5, SEQ ID NO:6 and SEQ ID NO:7. In certain embodiments, the four DNA oligonucleotides consist of a nucleic acid sequence independently having at least about 95%, 96%, 97%, 98%, 99% or 100% sequence identity to SEQ ID NO:1, SEQ ID NO:5, SEQ ID NO:6 and SEQ ID NO:7. In certain embodiments, a fluorophore or quencher is operably linked to SEQ ID NO:7. In certain embodiments, a fluorophore or quencher is operably linked to the 5' end of SEQ ID NO:7. In certain embodiments, a fluorophore or quencher is operably linked to the 3' end of SEQ ID NO:7. In certain embodiments, a quencher (e.g., BHQ-1) is operably linked to the 5' end of SEQ ID NO:7.

In certain embodiments, the DNA-tetrahedron is used to detect a dengue serotype 2 (DENV2) nucleic acid (e.g., RNA), and is formed from hybridization of four DNA oligonucleotides comprising at least about 75% sequence identity to SEQ ID NO:2, SEQ ID NO:5, SEQ ID NO:6 and SEQ ID NO:7. In certain embodiments, the four DNA oligonucleotides comprise nucleic acid sequences independently having at least about 95%, 96%, 97%, 98%, 99% or 100% sequence identity to SEQ ID NO:2, SEQ ID NO:5, SEQ ID NO:6 and SEQ ID NO:7. In certain embodiments, the four DNA oligonucleotides consist of a nucleic acid sequence independently having at least about 95%, 96%, 97%, 98%, 99% or 100% sequence identity to SEQ ID NO:2, SEQ ID NO:5, SEQ ID NO:6 and SEQ ID NO:7. In certain embodiments, a fluorophore or quencher is operably linked to SEQ ID NO:7. In certain embodiments, a fluorophore or quencher is operably linked to the 5' end of SEQ ID NO:7. In certain embodiments, a fluorophore or quencher is operably linked to the 3' end of SEQ ID NO:7. In certain embodiments, a quencher (e.g., BHQ-1) is operably linked to the 5' end of SEQ ID NO:7.

In certain embodiments, the DNA-tetrahedron is used to detect a dengue serotype 3 (DENV3) nucleic acid (e.g., RNA), and is formed from hybridization of four DNA oligonucleotides comprising at least about 75% sequence identity to SEQ ID NO:3, SEQ ID NO:5, SEQ ID NO:6 and SEQ ID NO:7. In certain embodiments, the four DNA oligonucleotides comprise nucleic acid sequences independently having at least about 95%, 96%, 97%, 98%, 99% or 100% sequence identity to SEQ ID NO:3, SEQ ID NO:5, SEQ ID NO:6 and SEQ ID NO:7. In certain embodiments, the four DNA oligonucleotides consist of a nucleic acid sequence independently having at least about 95%, 96%, 97%, 98%, 99% or 100% sequence identity to SEQ ID NO:3, SEQ ID NO:5, SEQ ID NO:6 and SEQ ID NO:7. In certain embodiments, a fluorophore or quencher is operably linked to SEQ ID NO:7. In certain embodiments, a fluorophore or quencher is operably linked to the 5' end of SEQ ID NO:7. In certain embodiments, a fluorophore or quencher is operably linked to the 3' end of SEQ ID NO:7. In certain embodiments, a quencher (e.g., BHQ-1) is operably linked to the 5' end of SEQ ID NO:7.

In certain embodiments, the DNA-tetrahedron is used to detect a dengue serotype 4 (DENV4) nucleic acid (e.g., RNA), and c is formed from hybridization of four DNA oligonucleotides comprising at least about 75% sequence identity to SEQ ID NO:4, SEQ ID NO:5, SEQ ID NO:6 and SEQ ID NO:7. In certain embodiments, the four DNA oligonucleotides comprise nucleic acid sequences independently having at least about 95%, 96%, 97%, 98%, 99% or 100% sequence identity to SEQ ID NO:4, SEQ ID NO:5, SEQ ID NO:6 and SEQ ID NO:7. In certain embodiments, the four DNA oligonucleotides consist of a nucleic acid sequence independently having at least about 95%, 96%, 97%, 98%, 99% or 100% sequence identity to SEQ ID NO:4, SEQ ID NO:5, SEQ ID NO:6 and SEQ ID NO:7. In certain embodiments, a fluorophore or quencher is operably linked to SEQ ID NO:7. In certain embodiments, a fluorophore or quencher is operably linked to the 5' end of SEQ ID NO:7. In certain embodiments, a fluorophore or quencher is operably linked to the 3' end of SEQ ID NO:7. In certain embodiments, a quencher (e.g., BHQ-1) is operably linked to the 5' end of SEQ ID NO:7.

Protector Oligonucleotide

As described herein, the protector oligonucleotide is operably linked to a quencher or a fluorophore and is capable of hybridizing to a single stranded region of the DNA-nanostructure, in a position that is suitable for quenching to occur between the fluorophore or quencher operably linked to the protector oligonucleotide and the fluorophore or quencher operably linked to the DNA-nanostructure.

The linkage between the protector oligonucleotide and the fluorophore/quencher is not critical, and may be any group that can connect the protector oligonucleotide and the fluorophore or quencher using known chemistry, provided that is does not interfere with the fluorescence and/or quenching or with the strand displacement. Certain embodiments of various fluorophores and quenchers are discussed below.

In certain embodiments, a fluorophore or quencher is operably linked to the 3'-end of the protector oligonucleotide. In certain embodiments, a fluorophore or quencher is operably linked to the 5'-end of the protector oligonucleotide.

In certain embodiments, a quencher is operably linked to the DNA-nanostructure and a fluorophore is operably linked to the protector oligonucleotide. In one embodiment, the fluorophore is operably linked to the 3' end of the protector oligonucleotide. In one embodiment, the fluorophore is a TET fluorophore and is operably linked to the 3' end of the protector oligonucleotide.

In one embodiment, the protector oligonucleotide is displaced by the viral nucleic acid but not by the capture oligonucleotide. Accordingly, in certain embodiments, the protector oligonucleotide is complementary to a single stranded region of the DNA-nanostructure and hybridizes to the second toehold but not the first toehold. In certain embodiments, the protector oligonucleotide comprises a sequence that has at least about 95, 96, 97, 98, 99 or 100% complementarity with a portion of the single stranded region of the DNA-nanostructure (i.e., the second toehold and an adjacent hybridization region).

In certain embodiments, the protector oligonucleotide is hybridized to a single-stranded region of the DNA-nanostructure, wherein the region of hybridization is linked to a toehold domain, and wherein the toehold domain is complementary to the viral nucleic acid. In certain embodiments, the region of hybridization includes a second toehold domain, and wherein the second toehold domain is complementary to the capture oligonucleotide.

The length of the protector oligonucleotide will depend on a variety of factors, including the size of the DNA-nanostructure and the sequence of the viral nucleic acid to be detected. In certain embodiments, the protector oligonucleotide is between about 10 to about 50 nucleotides in length. In certain embodiments, the protector oligonucleotide is between about 10 to about 40 nucleotides in length. In certain embodiments, the protector oligonucleotide is between about 10 to about 30 nucleotides in length. In certain embodiments, the protector oligonucleotide is between about 10 to about 25 nucleotides in length. In certain embodiments, the protector oligonucleotide is between about 15 to about 25 nucleotides in length. In certain embodiments, the protector oligonucleotide is between about 17 nucleotides in length. In certain embodiments, the protector oligonucleotide is between about 18 nucleotides in length. In certain embodiments, the protector oligonucleotide is between about 19 nucleotides in length.

In certain embodiments, a method of the disclosure is used to detect a DENV1 nucleic acid. In certain embodiments, the protector oligonucleotide comprises a nucleic acid sequence having at least about 75% sequence identity to SEQ ID NO:8. In certain embodiments, the protector oligonucleotide comprises a nucleic acid sequence having at least about 95%, 96%, 97%, 98%, 99% or 100% sequence identity to SEQ ID NO:8. In certain embodiments, the protector oligonucleotide consists of a nucleic acid sequence having at least about 95%, 96%, 97%, 98%, 99% or 100% sequence identity to SEQ ID NO:8.

In certain embodiments, a method of the disclosure is used to detect a DENV2 nucleic acid. In certain embodiments, the protector oligonucleotide comprises a nucleic acid sequence having at least about 75% sequence identity to SEQ ID NO:9. In certain embodiments, the protector oligonucleotide comprises a nucleic acid sequence having at least about 95%, 96%, 97%, 98%, 99% or 100% sequence identity to SEQ ID NO:9. In certain embodiments, the protector oligonucleotide consists of a nucleic acid sequence having at least about 95%, 96%, 97%, 98%, 99% or 100% sequence identity to SEQ ID NO:9.

In certain embodiments, a method of the disclosure is used to detect a DENV3 nucleic acid. In certain embodiments, the protector oligonucleotide comprises a nucleic acid sequence having at least about 75% sequence identity to SEQ ID NO:10. In certain embodiments, the protector oligonucleotide comprises a nucleic acid sequence having at least about 95%, 96%, 97%, 98%, 99% or 100% sequence identity to SEQ ID NO:10. In certain embodiments, the protector oligonucleotide consists of a nucleic acid sequence having at least about 95%, 96%, 97%, 98%, 99% or 100% sequence identity to SEQ ID NO:10.

In certain embodiments, a method of the disclosure is used to detect a DENV4 nucleic acid. In certain embodiments, the protector oligonucleotide comprises a nucleic acid sequence having at least about 75% sequence identity to SEQ ID NO:11. In certain embodiments, the protector oligonucleotide comprises a nucleic acid sequence having at least about 95%, 96%, 97%, 98%, 99% or 100% sequence identity to SEQ ID NO:11. In certain embodiments, the protector oligonucleotide consists of a nucleic acid sequence having at least about 95%, 96%, 97%, 98%, 99% or 100% sequence identity to SEQ ID NO:11.

In certain embodiments, a fluorophore is operably linked to the 3' end of the protector oligonucleotide (e.g., the 3' end of SEQ ID NO:8, SEQ ID NO:9, SEQ ID NO:10, or SEQ ID NO:11).

Capture Oligonucleotide

As described herein, in one embodiment, the capture oligonucleotide is capable of displacing the viral nucleic acid and hybridizing to the DNA-nanostructure but is not capable of displacing the protector oligonucleotide. Accordingly, in certain embodiments, the capture oligonucleotide is complementary to a single stranded region of the DNA-nanostructure and is capable of hybridizing to the second toehold (i.e., the viral nucleic acid is bound and the second toehold domain is accessible). In certain embodiments, the capture oligonucleotide comprises a sequence that has at least about 95, 96, 97, 98, 99 or 100% complementarity with a portion of the single stranded region of the DNA-nano-structure (i.e., the second toehold and the adjacent region wherein the viral nucleic acid is capable of hybridizing).

In certain embodiments, the capture oligonucleotide comprises a nucleic acid sequence that is complementary to a toehold domain in the DNA-nanostructure, wherein the toehold domain is linked to a nucleic acid sequence in the DNA-nanostructure that is capable of hybridizing to the viral nucleic acid.

The length of the capture oligonucleotide will depend on a variety of factors, including the size of the DNA-nano-structure and the sequence of the viral nucleic acid to be detected. In certain embodiments, the capture oligonucle-otide is between about 10 to about 50 nucleotides in length. In certain embodiments, the capture oligonucleotide is between about 10 to about 40 nucleotides in length. In certain embodiments, the capture oligonucleotide is between about 10 to about 30 nucleotides in length. In certain embodiments, the capture oligonucleotide is between about 15 to about 30 nucleotides in length. In certain embodiments, the capture oligonucleotide is between about 20 to about 27 nucleotides in length. In certain embodiments, the capture oligonucleotide is about 23 nucleotides in length. In certain embodiments, the capture oligonucleotide is about 24 nucleotides in length. In certain embodiments, the capture oligonucleotide is about 25 nucleotides in length.

In certain embodiments, a method of the disclosure is used to detect a DENV1 nucleic acid. In certain embodiments, the capture oligonucleotide comprises a nucleic acid sequence having at least about 75% sequence identity to SEQ ID NO:12. In certain embodiments, the capture oligo-nucleotide comprises a nucleic acid sequence having at least about 95%, 96%, 97%, 98%, 99% or 100% sequence identity to SEQ ID NO:12. In certain embodiments, the capture oligonucleotide consists of a nucleic acid sequence having at least about 95%, 96%, 97%, 98%, 99% or 100% sequence identity to SEQ ID NO:12.

In certain embodiments, a method of the disclosure is used to detect a DENV2 nucleic acid. In certain embodiments, the capture oligonucleotide comprises a nucleic acid sequence having at least about 75% sequence identity to SEQ ID NO:13. In certain embodiments, the capture oligo-nucleotide comprises a nucleic acid sequence having at least about 95%, 96%, 97%, 98%, 99% or 100% sequence identity to SEQ ID NO:13. In certain embodiments, the capture oligonucleotide consists of a nucleic acid sequence having at least about 95%, 96%, 97%, 98%, 99% or 100% sequence identity to SEQ ID NO:13.

In certain embodiments, a method of the disclosure is used to detect a DENV3 nucleic acid. In certain embodiments, the capture oligonucleotide comprises a nucleic acid sequence having at least about 75% sequence identity to SEQ ID NO:14. In certain embodiments, the capture oligo-nucleotide comprises a nucleic acid sequence having at least about 95%, 96%, 97%, 98%, 99% or 100% sequence identity to SEQ ID NO:14. In certain embodiments, the capture oligonucleotide consists of a nucleic acid sequence having at least about 95%, 96%, 97%, 98%, 99% or 100% sequence identity to SEQ ID NO:14.

In certain embodiments, a method of the disclosure is used to detect a DENV4 nucleic acid. In certain embodiments, the capture oligonucleotide comprises a nucleic acid sequence having at least about 75% sequence identity to SEQ ID NO:15. In certain embodiments, the capture oligonucleotide comprises a nucleic acid sequence having at least about 95%, 96%, 97%, 98%, 99% or 100% sequence identity to SEQ ID NO:15. In certain embodiments, the capture oligonucleotide consists of a nucleic acid sequence having at least about 95%, 96%, 97%, 98%, 99% or 100% sequence identity to SEQ ID NO:15.

Viral Nucleic Acid

As described herein, methods of the disclosure may be used to detect the presence of a viral nucleic acid in a sample. In one embodiment, the viral nucleic acid to be detected is capable of binding to the DNA-nanostructure and displacing the protector oligonucleotide, and as such, is complementary to a portion of the DNA-nanostructure (e.g., a single stranded portion of the nanostructure). In certain embodiments, the viral nucleic acid comprises a sequence that has at least about 80, 81, 82, 83, 84, 85, 86, 87, 88, 89, 90, 91, 92, 93, 94, 95, 96, 97, 98, 99 or 100% complementarity with a portion of a single stranded region of the DNA-nanostructure (i.e., at least one toehold and the region of the DNA-nanostructure to which the protector strand is hybridized). However, the viral nucleic acid does not hybridize with both the first and second toehold domain.

In certain embodiments, the viral nucleic acid is DNA.

In certain embodiments, the viral nucleic acid is RNA.

In certain embodiments, the viral nucleic acid is from any RNA or DNA virus, and these include, but are not limited to, flaviviruses (dengue virus, yellow fever virus, Zika virus, West Nile virus, tick borne encephalitis virus, and hepatitis C, among others), togaviruses (chikungunya virus, Mayaro virus, and Venezuelan equine encephalitis virus, among others), bunyaviruses (Hantavirus, Oropouche virus, and Rift Valley fever virus, among others), arenaviruses, filoviruses (Ebola viruses and Marburg virus), herpes viruses (cytomegalovirus, Epbstein-Barr virus, and human herpes viruses 1 and 2, among others), respiratory viruses (influenza, respiratory syncytial virus, parainfluenza viruses, and coronaviruses, among others), retroviruses [(human immunodeficiency virus (HIV) and human T-lymphotropic virus (HTLV)], and pox viruses (smallpox, monkeypox, and orf, among others).

In certain embodiments, the viral nucleic acid is from dengue virus. In certain embodiments, the viral nucleic acid is dengue RNA. In certain embodiments, the viral nucleic acid is from Dengue viral serotype 1 (DENV1). In certain embodiments, the DENV1 RNA comprises SEQ ID NO:16. In certain embodiments, the DENV1 RNA consists of SEQ ID NO:16. In certain embodiments, the viral nucleic acid is from Dengue viral serotype 2 (DENV2). In certain embodiments, the DENV2 RNA comprises SEQ ID NO:17. In certain embodiments, the DENV2 RNA consists of SEQ ID NO:17. In certain embodiments, the viral nucleic acid is from Dengue viral serotype 3 (DENV3). In certain embodiments, the DENV3 RNA comprises SEQ ID NO:18. In certain embodiments, the DENV3 RNA consists of SEQ ID NO:18. In certain embodiments, the viral nucleic acid is from Dengue viral serotype 4 (DENV4). In certain embodiments, the DENV4 RNA comprises SEQ ID NO:19. In certain embodiments, the DENV4 RNA consists of SEQ ID NO:19.

Fluorophore & Quencher

As described herein, the DNA-nanostructure is operably linked to a fluorophore and the protector oligonucleotide is operably linked to a quencher or the DNA-nanostructure is operably linked to a quencher and the protector oligonucleotide is operably linked to a fluorophore; and the quencher is capable of quenching the fluorescent light emitted from the fluorophore.

Chemical moieties that quench fluorescent light operate through a variety of mechanisms, including fluorescence resonance energy transfer (FRET) processes and ground state quenching. FRET is one of the most common mechanisms of fluorescent quenching and can occur when the emission spectrum of the fluorescent donor overlaps the absorbance spectrum of the quencher and when the donor and quencher are within a sufficient distance known as the Forster distance. The energy absorbed by a quencher can subsequently be released through a variety of mechanisms depending upon the chemical nature of the quencher. Captured energy can be released through fluorescence or through non-fluorescent mechanisms, including charge transfer and collisional mechanisms, or a combination of such mechanisms. When a quencher releases captured energy through non-fluorescent mechanisms FRET is simply observed as a reduction in the fluorescent emission of the fluorescent donor. Although FRET is the most common mechanism for quenching, any combination of molecular orientation and spectral coincidence that results in quenching is a useful mechanism for quenching. For example, ground-state quenching can occur in the absence of spectral overlap if the fluorophore and quencher are sufficiently close together to form a ground state complex.

Accordingly, the term "quenching" as used herein refers to the process wherein the quencher molecule absorbs energy from an excited fluorophore and then releases the captured energy through either fluorescent or non-fluorescent mechanisms. As used herein, the term "quencher" includes both molecules that do not emit any fluorescence signal ("dark quenchers"), as well as molecules that are themselves fluorophores and emit a signal ("fluorescent quenchers").

As discussed above, for quenching to occur, the fluorophore and quencher must be in physical proximity. When the fluorophore and quencher are separated (i.e., when the protector oligonucleotide is not hybridized to the DNA-nanostructure), energy absorbed by the fluorophore is no longer transferred to the quencher and is instead emitted as light at the wavelength characteristic of the fluorophore. Appearance/increase of a fluorescent signal from the fluorophore following removal of quenching is a detectable event and constitutes a "positive signal" in the assay of the present disclosure, and indicates the presence of a viral nucleic acid in a sample.

Specifically, detection agents that employ a fluorescent quencher will emit light both when the protector oligonucleotide is hybridized and unhybridized to the DNA-nanostructure; however, the wavelength of the light will differ depending on the hybridization state. In the hybridized state, energy captured by the fluorophore is transferred to the fluorescent quencher via FRET and is emitted as light at a wavelength characteristic of the fluorescent quencher. In the unhybridized state, the fluorophore and quencher are separated and energy absorbed by the fluorophore is no longer transferred to the quencher and is instead emitted as light at a wavelength characteristic of the fluorophore. In contrast, when the detection agent employs a dark quencher, a variation in the amount of fluorescent emission from the fluorophore will be observed depending on the hybridization state. In particular, when protector oligonucleotide is not hybridized to the DNA-nanostructure, energy absorbed by the fluorophore is emitted as light at a wavelength characteristic of the fluorophore. However, when the protector oligonucleotide is hybridized, energy captured by the dark quencher is released by non-fluorescent mechanisms, which appears as a reduction in the fluorescent emission from the fluorophore.

As discussed herein, quenching processes that rely on the interaction of two dyes as their spatial relationship changes can be used conveniently to detect the presence of a viral nucleic acids using a method described herein. As noted previously, the energy transfer process requires overlap between the emission spectrum of the fluorescent donor and the absorbance spectrum of the quencher. Therefore, quencher/fluorophore pairs may be selected by one skilled in the art based on their emission and absorbance spectrums to ensure sufficient quenching. For example, the quencher BHQ-1, which maximally absorbs light in the wavelength range of about 500-550 nm, can quench the fluorescent light emitted from the fluorophore fluorescein, which has a wavelength of about 520 nm. In contrast, the quencher BHQ-3, which maximally absorbs light in the wavelength range of about 650-700 nm would be less effective at quenching the fluorescence of fluorescein but would be quite effective at quenching the fluorescence of the fluorophore Cy5 which fluoresces at about 670 nm.

A fluorophore is a molecule that absorbs light (i.e., excites) at a characteristic wavelength and emits light (i.e., fluoresces) at a second lower-energy wavelength. Fluorescence reporter groups that can be operably linked to the DNA-nanostructure/protector oligonucleotide include, but are not limited to, fluorescein, tetrachlorofluorescein (TET), hexachlorofluorescein (HEX), tetramethylrhodamine (TRITC), rhodamine, cyanine-derivative dyes, Texas Red, Bodipy, and Alexa dyes. In certain embodiments, the fluorophore is TET. Characteristic absorption and emission wavelengths for each of these are well known to those of skill in the art.

A fluorophore may also be a fluorescent quencher, provided its absorbance spectrum overlaps with emission spectrum of the selected fluorophore donor (i.e., the fluorophore and fluorescent quencher are a FRET donor/acceptor pair). In certain embodiments, the quencher is selected from dabcyl, QSY™-7, QSY-33 (4',5-dinitrofluorescein, pipecolic acid amide) Black-Hole Quenchers (BHQ-)-1, -2, and -3. Additional quenchers are described in U.S. Pat. No. 7,439,341, which is incorporated by reference herein.

In certain embodiments, the fluorophore is TET and the quencher is BHQ-1.

Accordingly, in certain embodiments, the quencher is a fluorescent quencher.

As described herein, the fluorophore/quencher is operably linked to the DNA-nanostructure/protector oligonucleotide. The fluorophore and/or quencher may be conjugated directly to an oligonucleotide, or may be operably linked to the DNA-nanostructure/protector oligonucleotide by means of a linker.

Chemistries that can be used to link the fluorophores and quencher to an oligonucleotide are known in the art, such as disulfide linkages, amino linkages, covalent linkages, etc. In certain embodiments, aliphatic or ethylene glycol linkers that are well known to those with skill in the art can be used. In certain embodiments phosphodiester, phosphorothioate and/or other modified linkages are used. Modified covalent linkages include, but are not limited to, a phosphorothioate linkage, a phosphotriester linkage, a methyl phosphonate linkage, a methylene(methylimino) linkage, a morpholino linkage, an amide linkage, a polyamide linkage, a short chain alkyl intersugar linkage, a cycloalkyl intersugar linkage, a short chain heteroatomic intersugar linkage and a heterocyclic intersugar linkage.

In one embodiment, the fluorophore or quencher and the oligonucleotides are combined using 'click-chemistry' methods (Seo et al., 2003, J. Org. Chem, 68:609-612). Click chemistry reaction takes place between two components: azide and alkyne (terminal acetylene). For example, in one embodiment, the click chemistry reaction is a ring-strain promoted alkyne-azide cycloaddition reaction (SPAAC reaction) (Shelbourne et al. 2011, Chembiochem, 12: 1912-1921), or a copper-catalyzed alkyne-azide cycloaddition reaction (CuAAC reaction) (El-Sagheer et al. 2012, Acc Chem Res, 45(8): 1258-1267), catalyzed by Cu(I). Another embodiment uses a Diels-Alder reaction in which diene carrying oligonucleotides undergo cycloaddition with maleimide-terminated fluorescence dyes (Borsenberger et al., 2009, Nucleic Acids Res, 37(5): 1477-1485).

Modifications may be made at any position on the oligonucleotide, particularly the 3' position of the sugar on the 3' terminal nucleotide and the 5' position of 5' terminal nucleotide. Modifications of the 5' and 3' termini of an oligonucleotide may serve as points of chemical conjugation of a fluorophores or quencher.

A variety of chemical linkers may be used to conjugate an effector group to an oligonucleotide of the disclosure. As an example, U.S. Pat. No. 5,578,718 to Cook et al. discloses methods of attaching an alkylthio linker, which may be further derivatized to include additional groups, to ribofuranosyl positions, nucleosidic base positions, or on internucleoside linkages. Additional methods of conjugating oligonucleotides to various effector groups are known in the art; see, e.g., Protocols for Oligonucleotide Conjugates (Methods in Molecular Biology, Volume 26) Agrawal, S., ed., Humana Press, Totowa, N.J., 1994.

In certain embodiments, the linker is a binding pair. In certain embodiments, the "binding pair" refers to two molecules which interact with each other through any of a variety of molecular forces including, for example, ionic, covalent, hydrophobic, van der Waals, and hydrogen bonding, so that the pair have the property of binding specifically to each other. Specific binding means that the binding pair members exhibit binding to each other under conditions where they do not bind to another molecule. Examples of binding pairs are biotin-avidin, hormone-receptor, receptor-ligand, enzyme-substrate probe, IgG-protein A, antigen-antibody, and the like. In certain embodiments, a first member of the binding pair comprises avidin or streptavidin and a second member of the binding pair comprises biotin. Multiplex Assays for Differentiation of Viral Type or Serotype In one embodiment, the method of the disclosure relates to the use of two or more DNA-nanostructures specific for different viruses or different viral serotypes in a single reaction. In such an embodiment, the method may comprise contacting a sample with two or more DNA-nanostructures, wherein the two or more DNA-nanostructures are specific for different viruses or different viral serotypes. In such an embodiment, the two or more DNA-nanostructures may be bound to protector oligonucleotides which are operably linked to fluorophores with distinct emission spectra. For example, in one embodiment, the disclosure may comprise a method of detecting a DENV viral serotype comprising contacting a sample with a mixture of DNA-nanostructures wherein at least one DNA-nanostructure comprises a target hybridization domain that is specific for a DENV1 nucleic acid, at least one DNA-nanostructure comprises a target hybridization domain that is specific for a DENV2 nucleic acid, at least one DNA-nanostructure comprises a target hybridization domain that is specific for a DENV3 nucleic acid, and at least one DNA-nanostructure comprises a target hybridization domain that is specific for a DENV4 nucleic acid, wherein each of the DENV serotype specific DNA-nanostructures is hybridized to a protector oligonucleotide which is operably linked to a fluorophore, wherein the fluorophores are capable of being distinguished based on their emission spectra, allowing the identification of the viral serotype based on the emission of the dissociated protector oligonucleotide.

Multiple combinations of fluorescent molecule/quencher pairs can be used for differentiating between nanostructures when the nanostructures are used as a single assay. Exemplary fluorescent molecule/quencher pairs that can be used to differentially label the DNA nanostructures of the disclosure include, but are not limited to TET/BHQ1, FAM/BHQ1, Quasar 570/BHQ2, TAMRA/BHQ2, JOE/BHQ1, ROX/BHQ2, Biosearch Blue/BHQ1, HEX/BHQ1, NED/BHQ2; Cy3/BHQ2, Cy5/BHQ2, Cy5/BHQ3 6-FAM/BHQ1, Yakima Yellow/BHQ1, TEX 615/BHQ2, Alexa Fluor® 488/BHQ1, VIC®/BHQ1, PET™/BHQ2, and Alexa Fluor 594/BHQ2.

For example, in one embodiment the systems of the disclosure comprise the use of four DNA nanostructures, wherein each of the four DNA nanostructures and its associated protector oligonucleotide molecule are linked to a fluorescent molecule/quencher pair of TET/BHQ1, FAM/BHQ1, Quasar 570/BHQ2 and TAMRA/BHQ2 respectively. In one embodiment, each of four DNA nanostructures and its associated protector oligonucleotide molecule are linked to a fluorescent molecule/quencher pair of FAM/BHQ1, JOE/BHQ1, TAMRA/BHQ2 and ROX/BHQ2 respectively. In one embodiment, each of four DNA nanostructures and its associated protector oligonucleotide molecule are linked to a fluorescent molecule/quencher pair of Biosearch Blue/BHQ1, TET/BHQ1, HEX/BHQ1, and NED/BHQ2 respectively. In one embodiment, each of four DNA nanostructures and its associated protector oligonucleotide molecule are linked to a fluorescent molecule/quencher pair of TET/BHQ1, JOE/BHQ1, Cy3/BHQ2, Cy5/BHQ2 (BHQ3) respectively. In one embodiment, each of four DNA nanostructures and its associated protector oligonucleotide molecule are linked to a fluorescent molecule/quencher pair of 6-FAM/BHQ1, Yakima Yellow/BHQ1, Cy3/BHQ2, TEX 615/BHQ2 respectively. In one embodiment, each of four DNA nanostructures and its associated protector oligonucleotide molecule are linked to a fluorescent molecule/quencher pair of Alexa Fluor® 488/BHQ1, VIC®/BHQ1, PET™/BHQ2, Alexa Fluor 594/BHQ2 respectively. The above combinations are provided by way of example, however the disclosure is not limited to the specific combinations of fluorescent molecules/quenchers described as any combination and number of fluorescent molecules/quenchers can be used to multiplex DNA nanostructures of the disclosure provided that the emission spectra of the fluorescent molecules can be distinguished.

In one embodiment, the method of the disclosure relates to the use of two or more DNA-nanostructures specific for different viruses or different viral serotypes in a single assay, wherein the two or more DNA-nanostructures are spatially separated. For example, in one embodiment, the two or more DNA-nanostructures are localized to different, defined positions on a solid matrix (e.g., paper or other absorbent material capable of immobilizing the DNA nanostructure.) In one embodiment, the two or more DNA-nanostructures are localized to different wells of a multi-well assay plate. In such an embodiment, the disclosure may comprise a method of detecting a DENV viral serotype comprising contacting a sample, or an aliquot of a sample with multiple DNA-nanostructures simultaneously, in parallel or sequentially wherein at least one DNA-nanostructure comprises a target hybridization domain that is specific for a DENV1 nucleic acid, at least one DNA-nanostructure comprises a target hybridization domain that is specific for a DENV2 nucleic acid, at least one DNA-nanostructure comprises a target hybridization domain that is specific for a DENV3 nucleic acid, and at least one DNA-nanostructure comprises a target hybridization domain that is specific for a DENV4 nucleic acid, wherein each of the DENV serotype specific DNA-nanostructures is hybridized to a protector oligonucleotide which is operably linked to a fluorophore, wherein the fluorophores are capable of being distinguished based on their emission spectra, allowing the identification of the viral serotype based on the emission of the dissociated protector oligonucleotide.

Sample

The methods described herein may be used to detect the presence of viral nucleic acid in a sample, such as a biological fluid (e.g., present in molar, millimolar, micro-molar, nanomolar, picomolar, femtomolar, attomolar or sub-attomolar concentrations). Thus, in certain embodiments, the concentration of the viral nucleic acid in the sample is less than about, e.g., 1 millimole, 100 micromole, 10 micromole, 1 micromole, 100 nanomole, 10 nanomole, 1 nanomole, 100 picomole, 10 picomole, 1 picomole, 100 femtomole, 10 femtomole, 1 femtomole, 100 attomole, 10 attomole, 1 attomole or 0.1 attomole.

As used herein, a "sample" may be any sample potentially comprising a viral nucleic acid. In certain embodiments, the sample is a liquid sample. In certain embodiments, the sample is a biological sample obtained from a subject, such as a mammal. In certain embodiments, the sample is derived from a biological sample obtained from a subject, such as a mammal. Thus, certain embodiments of the disclosure, further comprise obtaining a biological sample from a subject. As described herein, the term "biological fluid" refers to any bio-organic fluid produced by an organism and includes, but is not limited to, e.g., amniotic fluid, aqueous humour, vitreous humour, bile, blood or components of blood (e.g., serum or plasma), milk, cerebrospinal fluid (CSF), endolymph, perilymph, feces, lymph, mucus, peri-cardial fluid, peritoneal fluid, pleural fluid, pus, serous fluid, semen, sputum, synovial fluid, sweat, urine, saliva, tears, vaginal secretions and vomit. In certain embodiments, the biological fluid is blood or a blood component, such as serum. In certain embodiments, a biological fluid is pro-cessed prior to performing an assay described herein. In certain embodiments, a biological fluid is not processed prior to performing an assay described herein.

Illustrative Compositions and Kits in Accordance with Certain Embodiments

Certain embodiments of the disclosure provide a DNA-nanostructure described herein (e.g., a DNA tetrahedron described herein). In certain embodiments, the DNA-nano-structure is a DNA-tetrahedron that comprises a fluorophore operably linked to one of the oligonucleotides. Certain embodiments of the disclosure provide a protector oligo-nucleotide described herein. Certain embodiments of the disclosure provide a detector agent described herein. Certain embodiments of the disclosure provide a capture oligonucle-otide described herein.

Certain embodiments of the disclosure provide a compo-sition comprising a detection agent described herein and a capture oligonucleotide described herein, and optionally, a buffer. In certain embodiments, the composition comprises a plurality of each of the components.

Certain embodiments of the disclosure provide a composition comprising a DNA-nanostructure described herein, a protector oligonucleotide described herein, and/or a capture oligonucleotide described herein. Certain embodiments of the disclosure provide a composition comprising a DNA-nanostructure described herein, a protector oligonucleotide described herein, and optionally, a capture oligonucleotide described herein. In certain embodiments, the composition further comprises a carrier. In certain embodiments, the composition comprises a plurality of each of the components.

Accordingly, certain embodiments of the disclosure provide a composition for detecting a viral nucleic acid in a sample, comprising: a DNA-nanostructure, a capture oligonucleotide and a protector oligonucleotide; wherein the DNA-nanostructure is operably linked to a fluorophore and the protector oligonucleotide is operably linked to a quencher or the DNA-nanostructure is operably linked to a quencher and the protector oligonucleotide is operably linked to a fluorophore; and wherein the quencher is capable of quenching the fluorescent light emitted from the fluorophore; wherein the protector oligonucleotide is capable of hybridizing to the DNA-nanostructure; wherein the viral nucleic acid is capable of displacing the protector oligonucleotide and hybridizing to the DNA-nanostructure; and wherein the capture oligonucleotide is capable of displacing the viral nucleic acid and hybridizing to the DNA-nanostructure but is not capable of displacing the protector oligonucleotide.

In certain embodiments, the DNA-nanostructure comprises at least one single stranded region. In certain embodiments, the single stranded region comprises a nucleic acid sequence that comprises a first toehold domain, a hybridization region and a second toehold domain. In certain embodiments, the first toehold domain comprises a nucleic acid sequence that is complementary to a portion of the viral nucleic acid. In certain embodiments, the protector oligonucleotide is not capable of hybridizing to the first toehold domain. In certain embodiments, the second toehold domain comprises a nucleic acid sequence that is complementary to a portion of the protector oligonucleotide and a portion of the capture oligonucleotide. In certain embodiments, the viral nucleic acid is not capable of hybridizing to the second toehold domain. In certain embodiments, the hybridization region comprises a nucleic acid sequence that is complementary to a portion of the viral nucleic acid, a portion of the protector oligonucleotide and a portion of the capture oligonucleotide.

In certain embodiments, the DNA-nanostructure is a DNA-tetrahedron. In certain embodiments, the DNA-tetrahedron comprises five double-stranded edges and one single stranded edge. In certain embodiments, the fluorophore/quencher is operably linked at the tetrahedron vertex, proximal to the single stranded edge. In certain embodiments, the DNA-tetrahedron comprises four oligonucleotides having at least about 95% sequence identity to SEQ ID NO:1, SEQ ID NO:5, SEQ ID NO:6 and SEQ ID NO:7. In certain embodiments, the DNA-tetrahedron comprises four oligonucleotides having at least about 95% sequence identity to SEQ ID NO:2, SEQ ID NO:5, SEQ ID NO:6 and SEQ ID NO:7. In certain embodiments, the DNA-tetrahedron comprises four oligonucleotides having at least about 95% sequence identity to SEQ ID NO:3, SEQ ID NO:5, SEQ ID NO:6 and SEQ ID NO:7. In certain embodiments, the DNA-tetrahedron comprises four oligonucleotides having at least about 95% sequence identity to SEQ ID NO:4, SEQ ID NO:5, SEQ ID NO:6 and SEQ ID NO:7.

In certain embodiments, the protector oligonucleotide is between about 15 to about 25 nucleotides in length. In certain embodiments, the fluorophore/quencher is operably linked to the 5' or 3' end of the protector oligonucleotide. In certain embodiments, the protector oligonucleotide comprises a nucleic acid sequence having at least about 95% sequence identity to SEQ ID NO:8, SEQ ID NO:9, SEQ ID NO:10 or SEQ ID NO:11.

In certain embodiments, the capture oligonucleotide is between about 15 to about 30 nucleotides in length. In certain embodiments, the capture oligonucleotide comprises a nucleic acid sequence that is complementary to a toehold domain in the DNA-nanostructure, and wherein the toehold domain is linked to a nucleic acid sequence in the DNA-nanostructure that is capable of hybridizing to the viral nucleic acid. In certain embodiments, the capture oligonucleotide comprises a nucleic acid sequence having at least about 95% sequence identity to SEQ ID NO:12, SEQ ID NO:13, SEQ ID NO:14 or SEQ ID NO:15.

In certain embodiments, the viral nucleic acid is from dengue virus, Ebola virus, human immunodeficiency virus (HIV), hepatitis B, hepatitis C, Influenza, SARS, measles, Zika, yellow fever, West Nile fever, smallpox, Marburg viruses, human papillomavirus, Kaposi's sarcoma-associated herpesvirus or human T-lymphotropic virus. In certain embodiments, viral nucleic acid is from Dengue virus. In certain embodiments, viral nucleic acid is from Dengue virus serotype 1, Dengue virus serotype 2, Dengue virus serotype 3, or Dengue virus serotype 4.

As described herein, methods of the disclosure may be used to detect viral nucleic acid in a sample. In certain embodiments, the viral nucleic acid is from dengue virus. The following embodiments describe DNA-nanostructures, protector oligonucleotides and capture oligonucleotides, which may be used to detect a dengue serotype-specific RNA using methods described herein.

Certain embodiments of the disclosure provide a system comprising a DNA-tetrahedron, a protector probe and a capture probe for detection of a DENV1 RNA. In one embodiment, the DENV1 RNA comprises a sequence of SEQ ID NO:16. In one embodiment the system comprises a DNA-tetrahedron formed from the hybridization of four oligonucleotides, wherein the oligonucleotides comprise SEQ ID NO:1, SEQ ID NO:5, SEQ ID NO:6 and SEQ ID NO:7 or variants thereof, wherein the variants are capable of hybridization to form a DNA tetrahedron structure, a protector oligonucleotide comprising a nucleotide sequence of SEQ ID NO:8, and a capture oligonucleotide comprising a nucleotide sequence of SEQ ID NO:12, and further wherein the DNA-nanostructure and the protector oligonucleotide are each operably linked to one of a quencher and a fluorophore pair, wherein the quencher is capable of quenching emission from the fluorophore when the fluorophore is held in proximity to the quencher through hybridization of the protector oligonucleotide to the DNA-tetrahedron structure.

Certain embodiments of the disclosure provide a system comprising a DNA-tetrahedron, a protector probe and a capture probe for detection of a DENV2 RNA. In one embodiment, the DENV2 RNA comprises a sequence of SEQ ID NO:17. In one embodiment the system comprises a DNA-tetrahedron formed from the hybridization of four oligonucleotides, wherein the oligonucleotides comprise SEQ ID NO:2, SEQ ID NO:5, SEQ ID NO:6 and SEQ ID NO:7 or variants thereof, wherein the variants are capable of hybridization to form a DNA tetrahedron structure, a protector oligonucleotide comprising a nucleotide sequence of SEQ ID NO:9, and a capture oligonucleotide comprising a nucleotide sequence of SEQ ID NO:13, and further wherein the DNA-nanostructure and the protector oligonucleotide are each operably linked to one of a quencher and a fluorophore pair, wherein the quencher is capable of quenching emission from the fluorophore when the fluorophore is held in proximity to the quencher through hybridization of the protector oligonucleotide to the DNA-tetrahedron structure.

Certain embodiments of the disclosure provide a system comprising a DNA-tetrahedron, a protector probe and a capture probe for detection of a DENV3 RNA. In one embodiment, the DENV3 RNA comprises a sequence of SEQ ID NO:17. In one embodiment the system comprises a DNA-tetrahedron formed from the hybridization of four oligonucleotides, wherein the oligonucleotides comprise SEQ ID NO:3, SEQ ID NO:5, SEQ ID NO:6 and SEQ ID NO:7 or variants thereof, wherein the variants are capable of hybridization to form a DNA tetrahedron structure, a protector oligonucleotide comprising a nucleotide sequence of SEQ ID NO:10, and a capture oligonucleotide comprising a nucleotide sequence of SEQ ID NO:14 and further wherein the DNA-nanostructure and the protector oligonucleotide are each operably linked to one of a quencher and a fluorophore pair, wherein the quencher is capable of quenching emission from the fluorophore when the fluorophore is held in proximity to the quencher through hybridization of the protector oligonucleotide to the DNA-tetrahedron structure.

Certain embodiments of the disclosure provide a system comprising a DNA-tetrahedron, a protector probe and a capture probe for detection of a DENV4 RNA. In one embodiment, the DENV4 RNA comprises a sequence of SEQ ID NO:19. In one embodiment the system comprises a DNA-tetrahedron formed from the hybridization of four oligonucleotides, wherein the oligonucleotides comprise SEQ ID NO:4, SEQ ID NO:5, SEQ ID NO:6 and SEQ ID NO:7 or variants thereof, wherein the variants are capable of hybridization to form a DNA tetrahedron structure, a protector oligonucleotide comprising a nucleotide sequence of SEQ ID NO:11, and a capture oligonucleotide comprising a nucleotide sequence of SEQ ID NO:15, and further wherein the DNA-nanostructure and the protector oligonucleotide are each operably linked to one of a quencher and a fluorophore pair, wherein the quencher is capable of quenching emission from the fluorophore when the fluorophore is held in proximity to the quencher through hybridization of the protector oligonucleotide to the DNA-tetrahedron structure.

In one embodiment, the disclosure relates to a system for differentially detecting viral serotype using at least 2, 3, or 4 or more DNA tetrahedrons of the disclosure. For example, in one embodiment, the disclosure relates to a system comprising four DNA-tetrahedrons for differentially detecting DENV viral serotype. In one embodiment, the system comprises a first DNA tetrahedron comprising a target hybridization domain specific for hybridizing to a DENV1 RNA, a second DNA tetrahedron comprising a target hybridization domain specific for hybridizing to a DENV2 RNA, a third DNA tetrahedron comprising a target hybridization domain specific for hybridizing to a DENV3 RNA, and a fourth DNA tetrahedron comprising a target hybridization domain specific for hybridizing to a DENV4 RNA. In one embodiment, the system further comprises at least 2, 3, or 4 or more protector oligonucleotides and at least 2, 3, or 4 or more capture oligonucleotide, wherein each DNA-nanostructure and it associated protector oligonucleotide are each operably linked to one of a quencher and a fluorophore pair, wherein the quencher is capable of quenching emission from the fluorophore when the fluorophore is held in proximity to the quencher through hybridization of the protector oligonucleotide to the DNA-tetrahedron structure, and further wherein each of the DNA-nanostructures or each of the protector oligonucleotides are linked to fluorophores that are distinguishable from each other based on their emission spectra.

Kits

The present disclosure further provides kits for practicing the present methods. Accordingly, certain embodiments of the disclosure provide a kit for detecting viral nucleic acid in a sample comprising:
 a) a DNA-nanostructure;
 b) a protector oligonucleotide;
 c) a capture oligonucleotide; and
 d) instructions for use;
wherein the DNA-nanostructure is operably linked to a fluorophore and the protector oligonucleotide is operably linked to a quencher or the DNA-nanostructure is operably linked to a quencher and the protector oligonucleotide is operably linked to a fluorophore; and wherein the quencher is capable of quenching the fluorescent light emitted from the fluorophore; wherein the protector oligonucleotide is capable of hybridizing to the DNA-nanostructure; wherein the viral nucleic acid is capable of displacing the protector oligonucleotide and hybridizing to the DNA-nanostructure; and wherein the capture oligonucleotide is capable of displacing the viral nucleic acid and hybridizing to the DNA-nanostructure but is not capable of displacing the protector oligonucleotide.

In certain embodiments, the kit comprises a DNA-nanostructure described herein (e.g., a DNA-tetrahedron described herein). In certain embodiments, the kit comprises a protector oligonucleotide as described herein. In certain embodiments, the kit comprises a capture oligonucleotide as described herein. In certain embodiments, the kit comprises a quencher described herein (e.g., a dark quencher or a fluorescent quencher). Such kits may optionally contain one or more of: a positive and/or negative control, RNase-free water, and one or more buffers. In certain embodiments, a kit may further include RNase-free laboratory plasticware (e.g., a plate(s), such a multi-well plate(s), such as a 96 well plate(s), a petri dish(es), a test tube(s), a cuvette(s), a plate(s) for fluorescence or luminescence etc.).

Any kit of the disclosure may also include suitable storage containers, e.g., ampules, vials, tubes, etc., for each reagent disclosed herein. The reagents may be present in the kits in any convenient form, such as, e.g., in a solution or in a powder form. The kits may further include a packaging container, optionally having one or more partitions for housing the various reagents.

Illustrative Methods in Accordance with Certain Embodiments

Certain embodiments of the disclosure provide a method for detecting at least one viral nucleic acid in a sample, comprising:
 a) contacting the sample with at least one detection agent and at least one capture oligonucleotide under conditions suitable for strand displacement, wherein the detection agent comprises a protector oligonucleotide hybridized to a DNA-nanostructure;
 wherein the DNA-nanostructure is operably linked to a fluorophore and the protector oligonucleotide is operably linked to a quencher or the DNA-nanostructure is operably linked to a quencher and the protector oligonucleotide is operably linked to a fluorophore; and wherein the quencher is capable of quenching the fluorescent light emitted from the fluorophore;
 wherein the viral nucleic acid is capable of displacing the protector strand and hybridizing to the DNA-nanostructure (i.e., and thereby disrupting the quenching between the quencher and the fluorophore); and
 wherein the capture oligonucleotide is capable of displacing the viral nucleic acid and hybridizing to the DNA-nanostructure but is not capable of displacing the protector oligonucleotide; and
 b) measuring the fluorescent emission from the fluorophore, wherein an increase in fluorescent emission indicates the presence of a viral nucleic acid (e.g., as compared to a control, such as the fluorescent emission of the detection agent prior to being contacted with the sample or a sample comprising no viral nucleic acid).

In certain embodiments of the disclosure, it is desirable to assay the sample in parallel with a control sample, which comprises a predetermined amount of the viral nucleic acid.

Accordingly, certain embodiments of the disclosure provide a method for detecting a viral nucleic acid in a test sample, comprising:

a) contacting the test sample with a first detection agent and a first capture oligonucleotide under conditions suitable for strand displacement;

b) contacting a control sample comprising a predetermined amount of viral nucleic acid with a second detection agent and a second capture oligonucleotide under conditions suitable for strand displacement;

wherein each detection agent comprises a protector oligonucleotide hybridized to a DNA-nanostructure;

wherein each DNA-nanostructure is operably linked to a fluorophore and each protector oligonucleotide is operably linked to a quencher or each DNA-nanostructure is operably linked to a quencher and each protector oligonucleotide is operably linked to a fluorophore; and wherein the quencher is capable of quenching the fluorescent light emitted from the fluorophore;

wherein the viral nucleic acid is capable of displacing the protector oligonucleotide and hybridizing to the DNA-nanostructure; and wherein the capture oligonucleotide is capable of displacing the viral nucleic acid and hybridizing to the DNA-nanostructure but is not capable of displacing the protector oligonucleotide; and c) measuring the fluorescent emission from the fluorophore in the test sample and in the control sample, wherein the relative fluorescence in the test sample as compared to the control sample indicates the presence or absence of the viral nucleic acid. In certain embodiments, the control sample is a negative control, and therefore, the predetermined amount of viral nucleic acid in the control sample is no viral nucleic acid. In such an embodiment, a fluorescent emission in the test sample that is greater than the fluorescent emission in the control sample indicates that the test sample comprises viral nucleic acid.

In certain embodiments, the fluorescent emission from the fluorophore in the test sample is at least about 1-100% greater than the fluorescent emission in the control sample (i.e., a negative control sample).

Methods of the disclosure may also be used to diagnose a mammal with a viral infection. Thus, certain embodiments of the disclosure provide, a method for diagnosing a mammal with a viral infection comprising:

a) detecting the presence of a viral nucleic acid in a sample obtained from the mammal by:

1) contacting the sample with a detection agent and a capture oligonucleotide under conditions suitable for strand displacement, wherein the detection agent comprises a protector oligonucleotide hybridized to a DNA-nanostructure;

wherein the DNA-nanostructure is operably linked to a fluorophore and the protector oligonucleotide is operably linked to a quencher or the DNA-nanostructure is operably linked to a quencher and the protector oligonucleotide is operably linked to a fluorophore; and wherein the quencher is capable of quenching the fluorescent light emitted from the fluorophore;

wherein the viral nucleic acid is capable of displacing the protector oligonucleotide and hybridizing to the DNA-nanostructure; and wherein the capture oligonucleotide is capable of displacing the viral nucleic acid and hybridizing to the DNA-nanostructure but is not capable of displacing the protector oligonucleotide; and 2) measuring the fluorescent emission from the fluorophore, wherein an increase in fluorescent emission as compared to a control indicates the presence of a viral nucleic acid; and b) diagnosing the mammal with a viral infection when the presence of the viral nucleic acid is detected.

In certain embodiments, the methods of the disclosure further comprise administering a treatment or therapeutic agent to the diagnosed mammal. As used herein, the term "therapeutic agent" includes agents that provide a therapeutically desirable effect when administered to an animal (e.g., a mammal, such as a human). The agent may be of natural or synthetic origin. For example, it may be a nucleic acid, a polypeptide, a protein, a peptide, or an organic compound, such as a small molecule. The term "small molecule" includes organic molecules having a molecular weight of less than about, e.g., 1000 amu. In one embodiment a small molecule can have a molecular weight of less than about 800 amu. In another embodiment a small molecule can have a molecular weight of less than about 500 amu.

In certain embodiments, the treatment or therapeutic agent is an anti-viral agent. In certain embodiments, the treatment or therapeutic agent is an agent to treat or prevent a comorbid condition or complication of a virus.

In certain embodiments, the viral nucleic acid is from dengue virus, Ebola virus, human immunodeficiency virus (HIV), hepatitis B, hepatitis C, Influenza, SARS, measles, Zika, yellow fever, West Nile fever, smallpox, Marburg viruses, human papillomavirus, Kaposi's sarcoma-associated herpesvirus or human T-lymphotropic virus and the anti-viral agent is useful for treating the particular viral infection. In certain embodiments, the viral infection is caused by a dengue virus and the treatment, therapeutic or anti-viral agent is useful for treating dengue virus fever, or a complication or comorbidity thereof. Exemplary treatments or therapeutic agents useful for treating dengue virus fever, include, but are not limited to, oral rehydration regimens and intravenous (IV) fluid therapy.

Therefore, in various embodiment, the methods of the disclosure may further comprise administering a therapeutic agent to a mammal (e.g., a mammal diagnosed with a particular disease, disorder or condition using a method described herein). In one embodiment, the disclosure may further comprise administration of an agent for treatment or prevention of one or more diseases or disorders associated with a viral infection. For example, in on embodiment, the disclosure may further comprise administration of an anti-viral agent, pre-exposure prophylaxis (PrEP), or a medication to reduce one or more symptom associated with a viral infection. Such a therapeutic agent may be formulated as pharmaceutical composition and administered to a mammalian host, such as a human patient in a variety of forms adapted to the chosen route of administration, e.g., orally or parenterally, by intravenous, intramuscular, topical or subcutaneous routes.

In certain embodiments, the sample is contacted with a composition comprising two or more detection agents (e.g., a plurality of detection agents) and two or more capture oligonucleotides (e.g., a plurality of capture oligonucleotides). In such an embodiment, a single viral nucleic acid may sequentially hybridize to a series of DNA-nanostructures and displace the protector oligonucleotides hybridized thereto. This recycling of the viral nucleic acid amplifies fluorescent emission and generates a stronger signal for detection.

In certain embodiments, a method of the disclosure further comprises incubating the sample, the detection agent and the capture oligonucleotide for a time sufficient for 1) any viral nucleic acid in the sample to hybridize to the DNA-nanostructure and to displace the protector oligonucleotide; 2) the capture reagent to hybridize to the DNA-nanostructure and to displace the viral nucleic acid; and 3)

optionally, to repeat steps 1-2 one or more times, so that the displaced viral nucleic acid may hybridize to an additional DNA-nanostructure and displace an additional protector oligonucleotide. For example, in certain embodiments, the sample, the detection agent and the capture oligonucleotide are incubated for about 5, 10, 15, 20, 25, 30, 35, 40, 45, 50, 55 or 60 minutes. In certain embodiments, the sample, the detection agent and the capture oligonucleotide are incubated for about 1, 2, 3, 4, 5, 6, 7, 8, 9, 10, 11, 12, 13, 14, 15, 16, 17, 18, 19, 20, 21, 22, 23, 24 or more hours. In certain embodiments, the sample, the detection agent and the capture oligonucleotide are incubated for about 3 hours. In certain embodiments, the sample, the detection agent and the capture oligonucleotide are incubated under a set of conditions described herein.

In certain embodiments, the sample, the detection agent and the capture oligonucleotide are contacted in the presence of a buffer solution (e.g., Tris-HCl—Mg$^{2+}$ buffer). As described herein, a "buffer solution" refers to an aqueous solution consisting of a mixture of a weak acid and its conjugate base, or vice versa, and its pH changes very little when a small amount of strong acid or base is added to it. Buffer solutions and buffering agents are known in the art.

In certain embodiments, the sample, the detection agent and the capture oligonucleotide are contacted at a pH 8.0.

In certain embodiments, the sample, the detection agent and the capture oligonucleotide are contacted at room temperature.

In certain embodiments, the sample, the detection agent and the capture oligonucleotide are contacted in the dark.

In certain embodiments, methods of the disclosure further comprise generating the detection agent, comprising contacting the DNA-nanostructure with the protector oligonucleotide under conditions suitable for hybridization to occur between the protector oligonucleotide and the DNA-nanostructure.

In certain embodiments, the methods further comprise obtaining a test sample (e.g., a biological sample) from a subject (e.g., a mammal, e.g., a human).

In certain embodiments, the methods further comprise exciting the fluorophore.

In certain embodiments, the methods further comprise quantifying the concentration of the viral nucleic acid in the sample.

EXPERIMENTAL EXAMPLES

The disclosure is further described in detail by reference to the following experimental examples. These examples are provided for purposes of illustration only, and are not intended to be limiting unless otherwise specified. Thus, the disclosure should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present disclosure and practice the claimed methods. The following working examples therefore, specifically point out exemplary embodiments of the present disclosure, and are not to be construed as limiting in any way the remainder of the disclosure.

Example 1: Selective Detection of Different Dengue Virus RNA Serotypes Using Tandem Toehold-Mediated Displacement Reactions In this study, an enzyme-free assay was developed for signal amplification and serotype-specific DENV detection at ambient temperatures. The goal is for this novel method to provide sensitive, serotype-specific DENV detection during the acute-phase and clinical evaluation of patients with dengue.

A new DNA tetrahedron was designed containing a quencher at one apex (FIG. 1). On the single-stranded edge of the tetrahedron, adjacent to the quencher, DENV serotype-specific, complementary DNA sequence were inserted used to detect viral RNA. At the baseline, or "off" state, a fluorophore-labeled protector DNA molecule was annealed to prevent nonspecific binding. Four serotype-specific DNA tetrahedrons were constructed to detect conserved sequences of the four serotypes of DENV and evaluated using synthesized nucleic acids and spiked clinical samples. After signal amplification via the tTMDR, the fluorescence was detected using a fluorescence scanner (Azure Imaging System) and a confocal microscope with a photon counts technique.

As described herein, the detection of DENV RNA was evaluated in 16 spiked clinical samples. Whole blood and plasma were spiked with cultured isolates of each DENV serotype to replicate viral loads observed in acute infection (Waggoner et al., 2017, J Infect Dis, 215:1816-1823; Waggoner et al., 2016, Clin Infect Dis, 63:1584-1590; Duyen et al., 2011, J Infect Dis, 203:1292-1300; Tricou et al., 2011, PLoS Negl Trop Dis, 5: e1309). The technology developed in this study was able to detect DENV RNA concentrations that were at least 100-fold lower than values commonly observed in first days of illness. Notably, the tTMDRs can be performed in any laboratory with capacity to read an ELISA plate, thereby expanding access to molecular testing.

Novel features in the tTMDR design serve to improve assay performance and make clinical testing for human arboviruses feasible. These features include use of a labeled protector DNA molecule and tTMDRs incorporated into a rigid DNA tetrahedral structure. A rigid three-dimensional structure provided by the tetrahedron constrains the orientation of the toehold sequence such that it is accessible to and can react with the target RNA. Following addition of target RNA and initiation of the reaction, the tandem toehold design creates a second TMDR that displaces target RNA from the tetrahedron and blocks the rehybridization of the labeled Protector DNA. This allows target RNA to be recycled and initiate multiple reactions, thereby significantly improving sensitivity.

Four different DNA tetrahedrons were designed and applied to distinguish the different serotypes of DENV RNA. Both the synthetic RNAs and genomic RNAs from extracted clinical samples were identified reliably using the enzyme-free, tTMDRs. This method is highly sensitive and specific for DENV and provides a novel method for the detection of human RNA viruses. Therefore, this technology expands on previous tTMDRs methods, providing the ability to identify the serotype of DENV.

The materials and methods used in these experiments are now described.

Materials and Reagents.

All DNA and RNA oligonucleotides were purchased from Integrated DNA Technologies, Inc. (Coralville, IA). The sequences are listed in Table 1. Magnesium chloride hexahydrate was purchased from Mallinckrodt Pharmaceuticals (St. Louis, MO), Tris base was purchased from Geno Technology, Inc. (St. Louis, MO), ammonium persulfate and N,N,N',N'-tetramethylethylenediamine (TEMED) were purchased from Sigma-Aldrich Co. (St. Louis, MO), and 40% acrylamide/bis-acrylamide solution was purchased from Thermo Fisher Scientific Inc. (Ward Hill, MA). All reagents are of analytical grade unless otherwise indicated. An analog vortex mixer (VWR, Radnor, PA) was used to mix the solutions and 18.2 MΩ·cm H$_2$O was used for all experiments.

TABLE 1

Sequences of the DNAs used in this study. The toeholds are shown in
italics. Recognition regions are shown in boldface. Amplification
regions are underlined

| Name | SEQ ID NO: | Sequence (5' to 3') | Modification | Base |
|---|---|---|---|---|
| Type1-DNA 1 | SEQ ID NO: 1 | TGCTCTTCCCGA*AAACAG*CATATTGACGCTGG *CAACTCCC*ACTCAACTG CCTGGTGATACGAGGA TGGGCA | N/A | 71 |
| Type2-DNA 1 | SEQ ID NO: 2 | TGCTCTTCCCGA*AAACATTT*CATGTTAGTTTT*G CCTTCTC*ACTCAACTGC CTGGTGATACGAGGAT GGGCA | N/A | 71 |
| Type3 DNA 1 | SEQ ID NO: 3 | TGCTCTTCCCGA*ACATGA*TGACTTCTTCTTTT*A ACGTCC*AACTCAACTGC CTGGTGATACGAGGAT GGGCA | N/A | 71 |
| Type4-DNA 1 | SEQ ID NO: 4 | TGCTCTTCCCGA*AGACAA*CCAAATCCTCTCTT*T TCCCTAC*ACTCAACTGC CTGGTGATACGAGGAT GGGCA | N/A | 71 |
| DNA 2 | SEQ ID NO: 5 | GGTGATAAAACGTGTA GCAAGCTGTAATCGAC GGGAAGAGCATGCCCA TCCACTACTATGGCG | N/A | 63 |
| DNA 3 | SEQ ID NO: 6 | AGGCAGTTGAGACGAA CATTCCTAAGTCTGAAA TTTATCACCCGCCATAG TAGACGTATCACC | N/A | 63 |
| DNA 4 | SEQ ID NO: 7 | TCGATTACAGCTTGCTA CACGATTCAGACTTAG GAATGTTCGT | 5'-BHQ-1 | 43 |
| Type 1-Protector DNA | SEQ ID NO: 8 | AGGCAAGAAGTCACTA | 3'-TET | 16 |
| Type 2-Protector DNA | SEQ ID NO: 9 | AAAACTAACATGAAAT | 3'-TET | 16 |
| Type 3-Protector DNA | SEQ ID NO: 10 | AAAAGAAGAAGTCATC | 3'-TET | 16 |
| Type 4-Protector DNA | SEQ ID NO: 11 | AAGAGAGGATTTGGTT | 3'-TET | 16 |
| Type 1-Capture DNA | SEQ ID NO: 12 | AACAAGGCAAGAAGTC ACTATCA | N/A | 23 |
| Type 2-Capture DNA | SEQ ID NO: 13 | AGGCAAAACTAACATG AAATGTT | N/A | 23 |
| Type 3-Capture DNA | SEQ ID NO: 14 | ACGTTAAAAGAAGAAG TCATCAT | N/A | 23 |
| Type 4-Capture DNA | SEQ ID NO: 15 | GGAAAAGAGAGGATTT GGTTGTC | N/A | 23 |

DNA Stock Solutions.

The purchased oligonucleotides were dissolved in 10 mM Tris-HCl buffer, pH 8.0, with 10 mM $Mg^{2+}$ (referred to as TH—Mg buffer) and stored at −4° C. TH—Mg buffer was used as the reaction buffer throughout.

Annealing.

The annealing processes were performed using a dry bath incubator (Boekel Scientific, Feasterville, PA.). The solution of mixed DNAs was heated to 95° C. for 15 minutes and then allowed to cool to room temperature over a period over 2 hours. The annealed DNA complex solution was stored at 4° C.

Characterization of the DNA Tetrahedron.

The DNA tetrahedron was synthesized with DNAs 1, 2, 3, 4 and Protector DNA by an annealing process described previously (Zhang et al., 2017, Chem Commun 53:573-576; Gao et al., 2018, Chem Commun 54:968-971). The DNA sequences used to prepare all of the DNA tetrahedron are listed in Table 1. Native polyacrylamide gel electrophoresis (5% PAGE) was used to characterize the formation of the DNA tetrahedron. A DNA sequencing system (Model 4200, Fotodyne, Hartland, WI) was used to supply the constant direct current. The voltage was set at 80 V while the power was less than 3 W to minimize any change in temperature. Normally, the electrophoresis was complete within 90 minutes.

Characterization of Toehold-Mediated Displacement Reaction Using a Fluorescence Spectrometer.

To 100 nM DNA tetrahedron was added 10 nM target RNA and 100 μM Capture DNA. TH—Mg buffer was used to adjust the volume to 100 μL. The reaction was maintained at room temperature for 3 hours in the dark and the fluorescence was measured. The synthetic RNA sequences were listed in Table 2.

Calculation of Relative Recovery Efficiency.

The relative recovery efficiency ($\eta$) was determined using the average photon counts within 5 seconds, and is described by following equation, $$\eta = \frac{\overline{N}_{sample} - \overline{N}_{background}}{\overline{N}_{background}} \qquad (2)$$

where the $\overline{N}_{sample}$ is the average photon counts of the sample and the $\overline{N}_{background}$ is the average photon counts of the background.

Experimental Setup for Single Molecule Detection.

Single molecule detection was performed on a Nikon inverted TE2000-U microscope (Nikon Instruments Inc., Melville, NY). A krypton/argon laser (Melles Griot 35-KAP-431-208, IDEX Health & Science LLC., Carlsbad, CA) was used as the excitation source for all experiments. The laser beam was reflected by a double dichroic mirror (514 nm/647 nm, Chroma Tech. Co., Bellows Falls, VT) and focused by a water immersion 60×/1.20 Plan-Apo objective lens (Nikon Instruments Inc., Melville, NY) to excite the samples on the cover glasses (Fisher Scientific International, Inc., Asheville, NC). Emitted photons were collected using the same objective lens. The collected photons were then focused through a 100 micron confocal pinhole and filtered through a 525 nm long-pass emission filter. A single photon counting APD (avalanche photodiode) (τ-SPAD, PicoQuant, Germany) detected the signal which was subsequently processed using a 6602 counter/timer module (National Instruments, Austin, TX). The power of the laser was set at 0.1 mW to minimize photo-bleaching of the organic fluorescent dyes, and the signal was integrated for 5 seconds.

Preparation of Spiked Clinical Samples.

Spiked samples were prepared by adding cultured DENV strains to pooled, DENV-negative whole blood and plasma.

TABLE 2

| SEQ ID NO: | Name | Source | Version | Sequence | Starting Position | Base |
|---|---|---|---|---|---|---|
| | Sequences of the synthetic RNAs used in this study | | | | | |
| SEQ ID NO: 16 | Type-1 RNA | Dengue Virus 1 | M87512.1 | AAAUCAAAC AAGGCAAGA AGUCAGGC | 10288 | 26 |
| SEQ ID NO: 17 | Type-2 RNA | Dengue Virus 2 | M20558.1 | GGUAGAAGG CAAAACUAA CAUGAAAC | 10268 | 26 |
| SEQ ID NO: 18 | Type-3 RNA | Dengue Virus 3 | M93130.1 | CAAGGACGU UAAAAGAAG AAGUCAGG | 10351 | 26 |
| SEQ ID NO: 19 | Type-4 RNA | Dengue Virus 4 | M14931.2 | ACCUAGGGA AAAGAGAGG AUUUGUGG | 10078 | 26 |

Calculation of Total Quenching Efficiency.

The quenching efficiency of fluorescence was contributed by both radiative, non-radiative decay and FRET (Zou et al., 2015, Analyst 140:4121-4129); it is referred to as the total quenching efficiency ($\eta$_total) and can be described as:

$$\eta_q = 1 - \frac{I_N}{I_0} \qquad (1)$$

where the $I_N$ is the fluorescent intensity of P-TH and $I_0$ is the fluorescent intensity of TET-labeled Protector DNA.

The DENY strains included the following: DENV-1 (Hawaii), DENV-2 (New Guinea C), DENV-3 (Sleman/78) and DENV-4 (H241). Culture supernatants were obtained. Two concentrations of each sample type and serotype were prepared and tested (16 samples in total). Concentrations were made to mimic a normal-to-high viral load as well as 100-fold dilution of this concentration. Total nucleic acids were then extracted from 50 μL of whole blood or 200 μL of plasma from each sample using an eMAG instrument (Biomerieux, Durham, NC). Nucleic acids were eluted into 50 μL of buffer and stored at −80° C. until use.

Detecting Dengue Viral RNA.

The clinical samples were diluted in 100 times with 1 mM Tris-HCl buffer, pH 8.0, containing 1 mM $Mg^{2+}$ for further use. In a typical reaction, 5 μL of 100 nM DNA tetrahedron corresponding to a specific dengue viral RNA, 1 μL of 10 mM Tris-HCl buffer, pH 8.0, containing 10 mM $Mg^{2+}$, 0.4 μL of 1 μM Capture DNA and 1 μL of the prepared clinical sample were added, then $H_2O$ was added to increase the volume to 10 μL. The reaction mixture was maintained in the dark for 6 hours and then used for fluorescence and FCS measurements.

The results of the experiments are now described.

Assay Design.

Four DNA tetrahedrons were designed, each constructed of four DNA oligonucleotides as the basic structure. All of the tetrahedrons had five edges comprising 20 bp double-strand DNA and one edge with a 28 nt single-strand DNA. A black hole quencher 1 (BHQ-1) was attached at the apex of the DNA tetrahedron adjacent to the single strand. To form the tTMDR, a Protector DNA, which was labelled with a fluorescent dye tetrachlorofluorescein (TET) at its 3'-end, was annealed to each tetrahedron. An eight nucleotide (nt) DNA sequence on the single strand of the tetrahedron adjacent to the Protector DNA served as the first toehold. In the absence of target RNA, the fluorescence of TET was quenched by the BHQ-1 on the tetrahedron. In the presence of the target RNA, it annealed to the first toehold and displaced the Protector DNA base-by-base (Zhang and See-lig, 2011, Nat Chem, 3:103-113; Zhang et al., 2007, Science, 318:1121-1125; Yurke et al., 2000, Nature, 406:605-608). Once the Protector DNA had been displaced, the fluorescence was recovered since the donor and acceptor were no longer in spatial proximity. With the displacement of DENV RNA, the other 8-nt toehold beyond the 5'-end of the target sequence (the tandem toehold) was exposed and annealed to a Capture DNA present in the solution. The second toehold-mediated displacement reaction released the target RNA. The released target RNA was thus "recycled", making it available for the displacement of the Protector DNA on another DNA tetrahedron, thus further amplifying the fluorescence signal. Binding of Capture DNA prevents rean-nealing of Protector DNA to the same tetrahedron, which preserves the signal throughout the reaction.

DNA Tetrahedron.

Figures 2A, 2B:
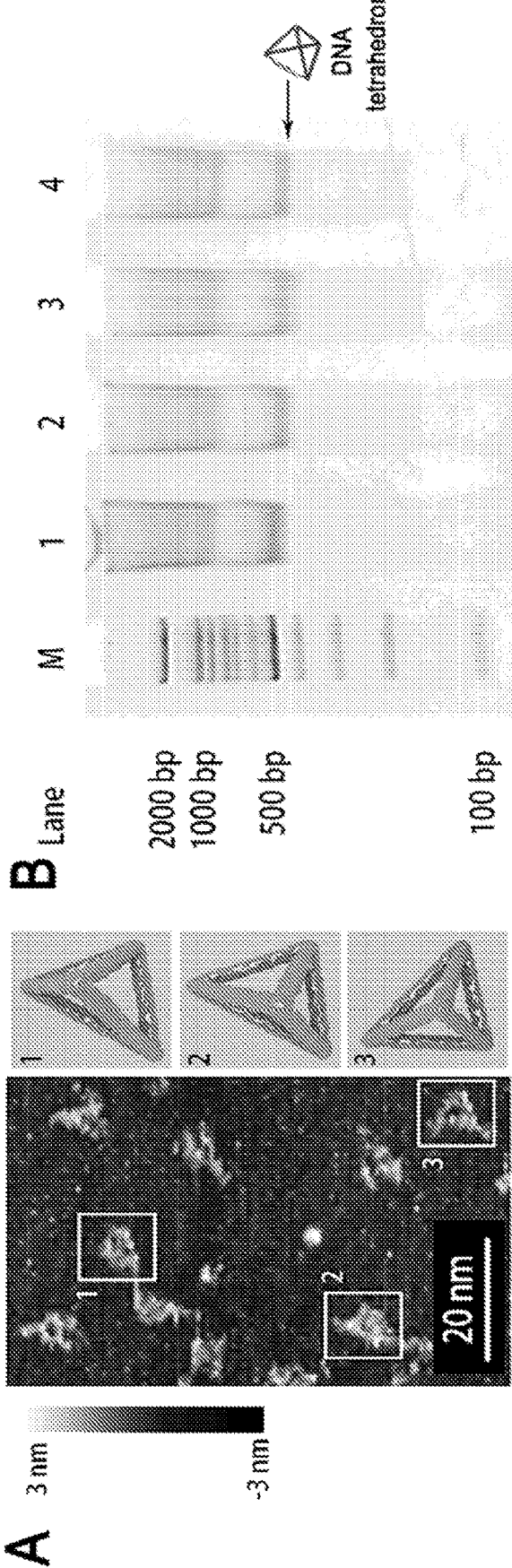
FIG. 2A and FIG. 2B depict the confirmation of the formation of DNA tetrahedrons.

The formation of the DNA tetrahedron was confirmed both by atomic force microscope (AFM) and native poly-acrylamide gel electrophoresis (PAGE). The DNA tetrahe-dron for the detection of DENV-1 was deposited on mica for the AFM test. As depicted in the image presented in FIG. 2A, the tetrahedron was manifested as uniform, triangle-like spots with a maximum linear dimension of ~8-9. The 3D reconstruction indicated possible orientations for the corre-sponding spots. PAGE also indicated the formation of four DNA tetrahedrons for detection of the four serotypes of dengue virus, respectively (FIG. 2B).

Analytical Evaluation.

Figure 3A:
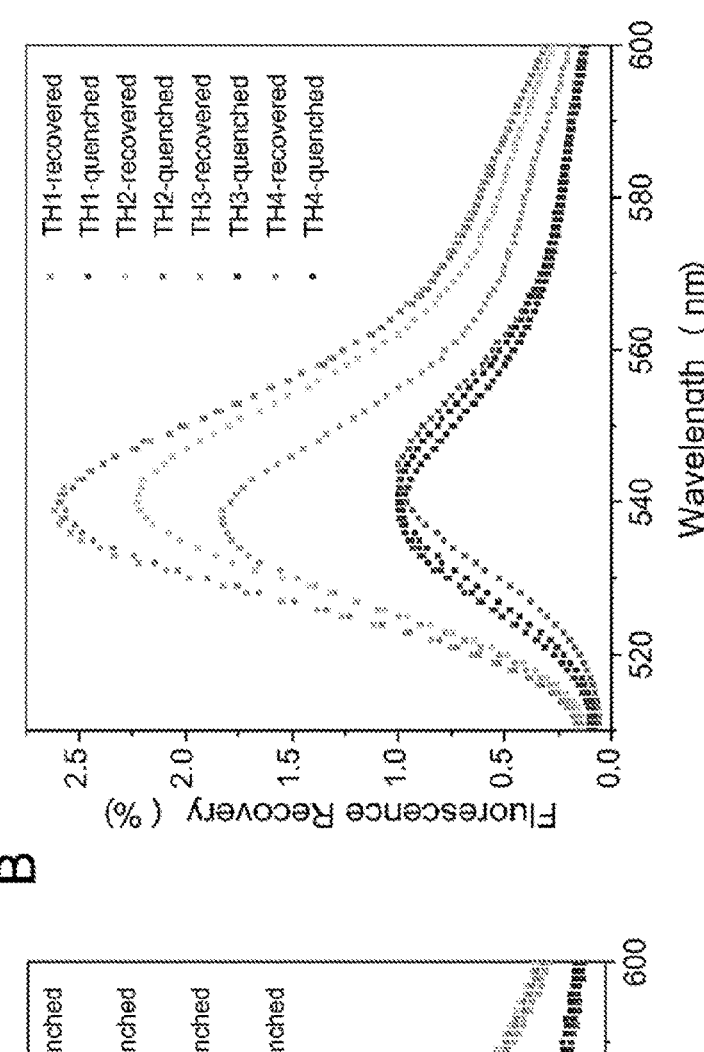
FIG. 3A and FIG. 3B depict the fluorescence spectra of four DNA tetrahedrons.
Figure 3B:
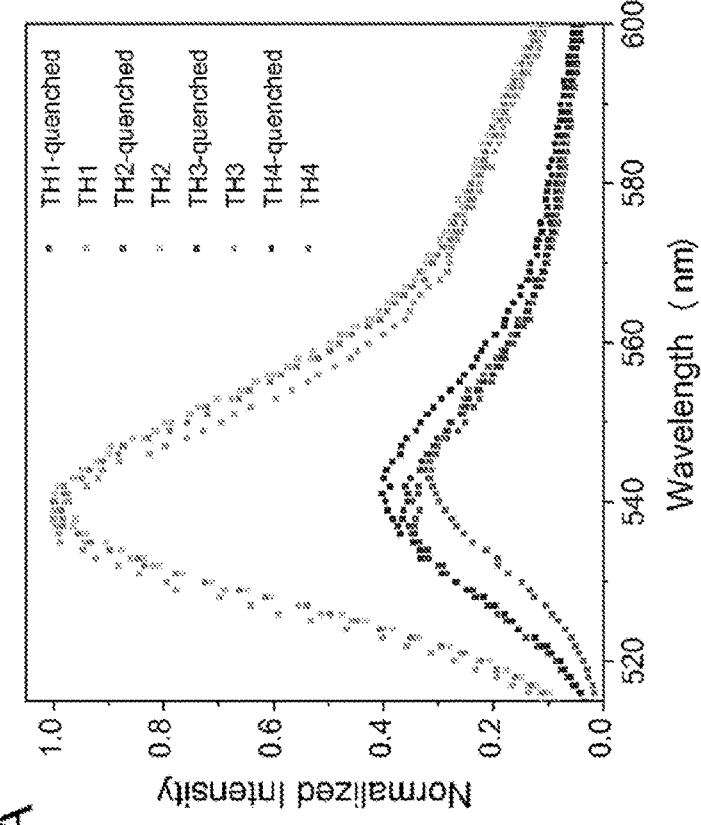

The ability of each DNA tetrahedron to detect DENV RNA was evaluated. The distance between the fluorescent dye TET and quencher BHQ-1 was fixed by the structure, and the quenching efficiencies of the four tetrahedrons were all around 65% (FIG. 3A), consistent with other published reports and calculations (Gao et al., 2018, Chem Commun (Camb), 54:968-971). To ensure the occurrence of tTMDRs on each tetrahedron, four synthetic RNAs were added to their corresponding tetrahedrons, respectively, to recover the fluorescence. After the tTMDRs had taken place, the fluo-rescence was recovered about 1.8-2.6 fold for all these RNAs (FIG. 3B).

Figure 4A:
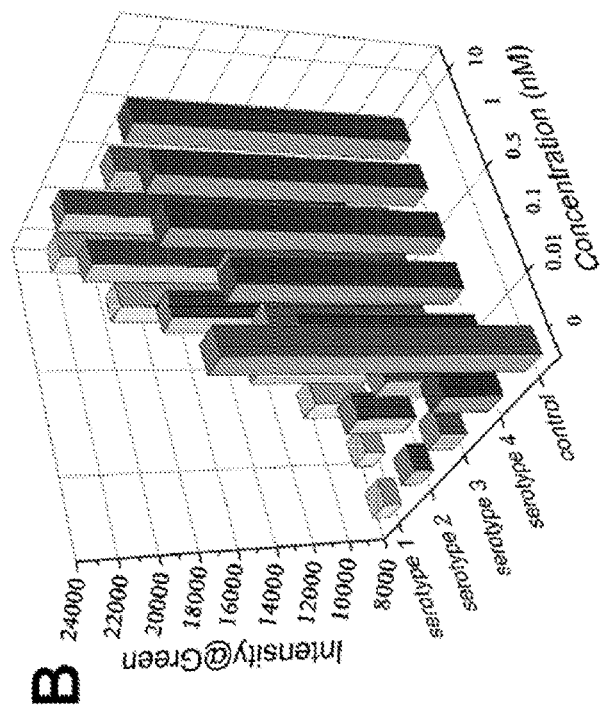
FIG. 4A and FIG. 4B depict the fluorescence detection of four synthetic RNAs with DNA tetrahedrons.
Figure 4B:
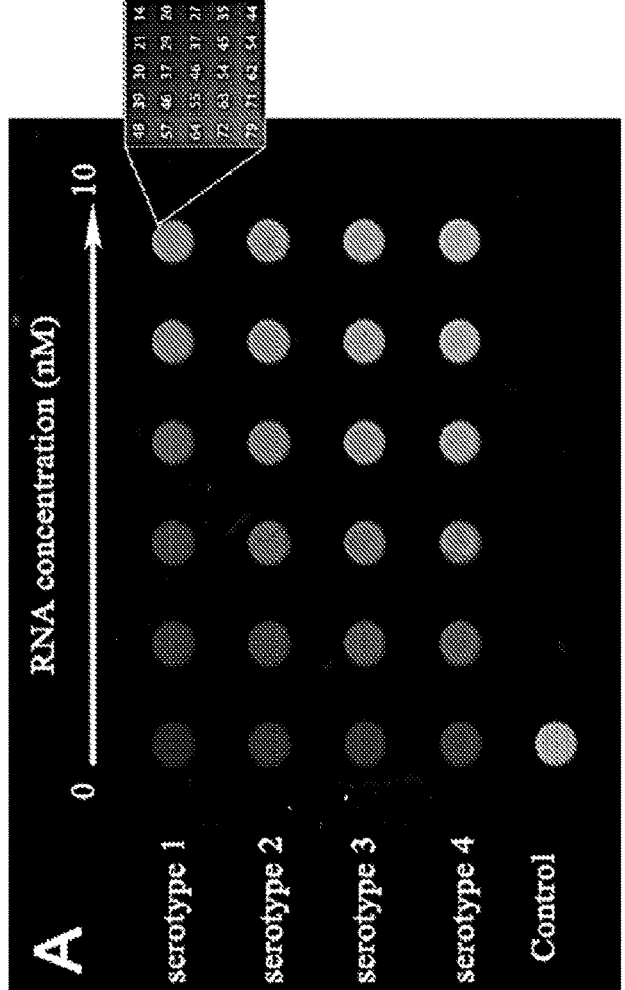
Figure 6A:
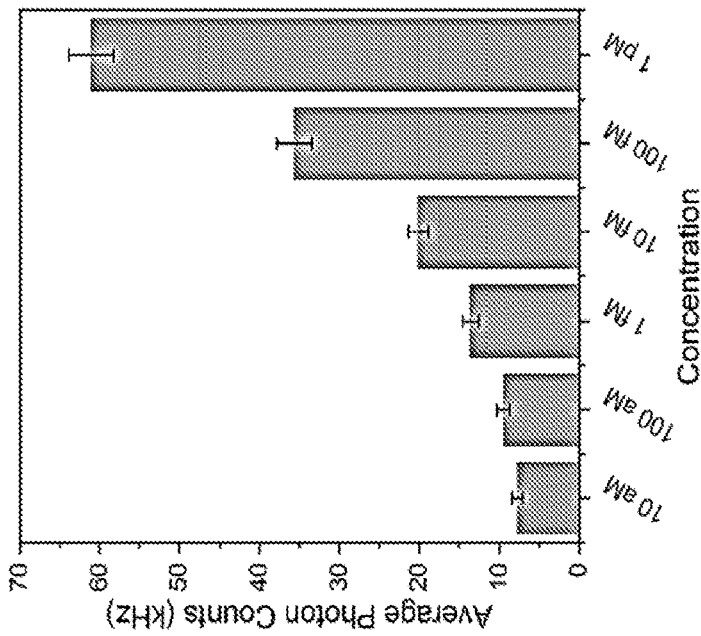
FIG. 6A depicts an exemplary photon count rate of the serotype 2 DNA tetrahedron in the presence of different concentrations of serotype 2 synthetic dengue viral RNA.
Figure 6B:
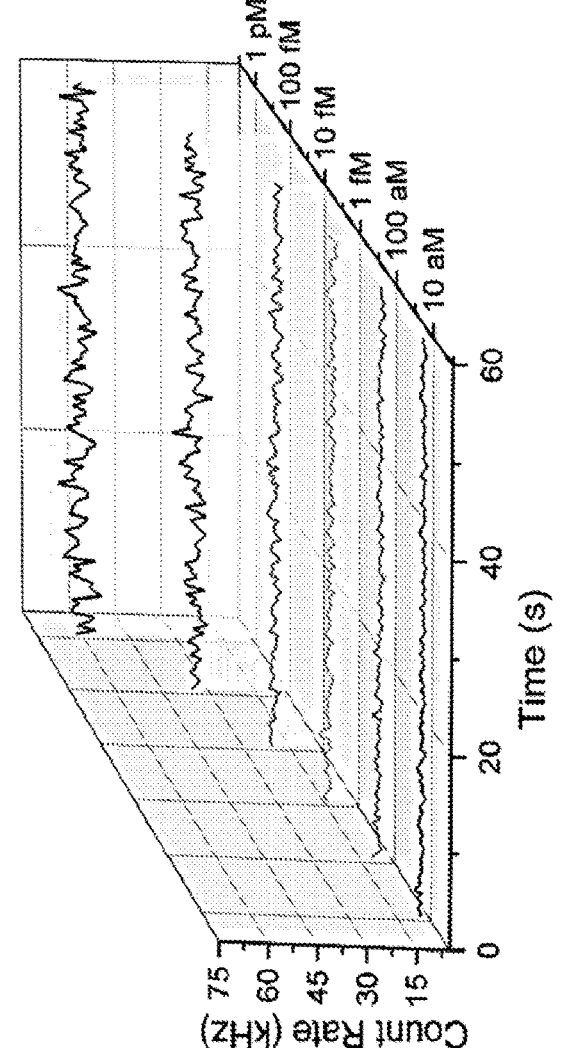
FIG. 6B depicts an exemplary histogram of average photon counts of serotype 2 DNA tetrahedron in the presence of different concentration of serotype 2 synthetic dengue viral RNA after 60 seconds.
Figure 7A:
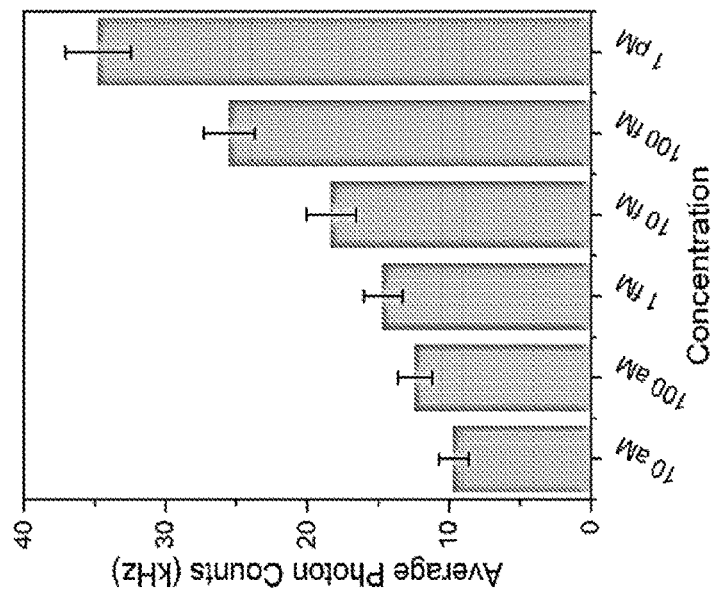
FIG. 7A depicts an exemplary photon count rate of the serotype 3 DNA tetrahedron in the presence of different concentrations of serotype 3 synthetic dengue viral RNA.
Figure 7B:
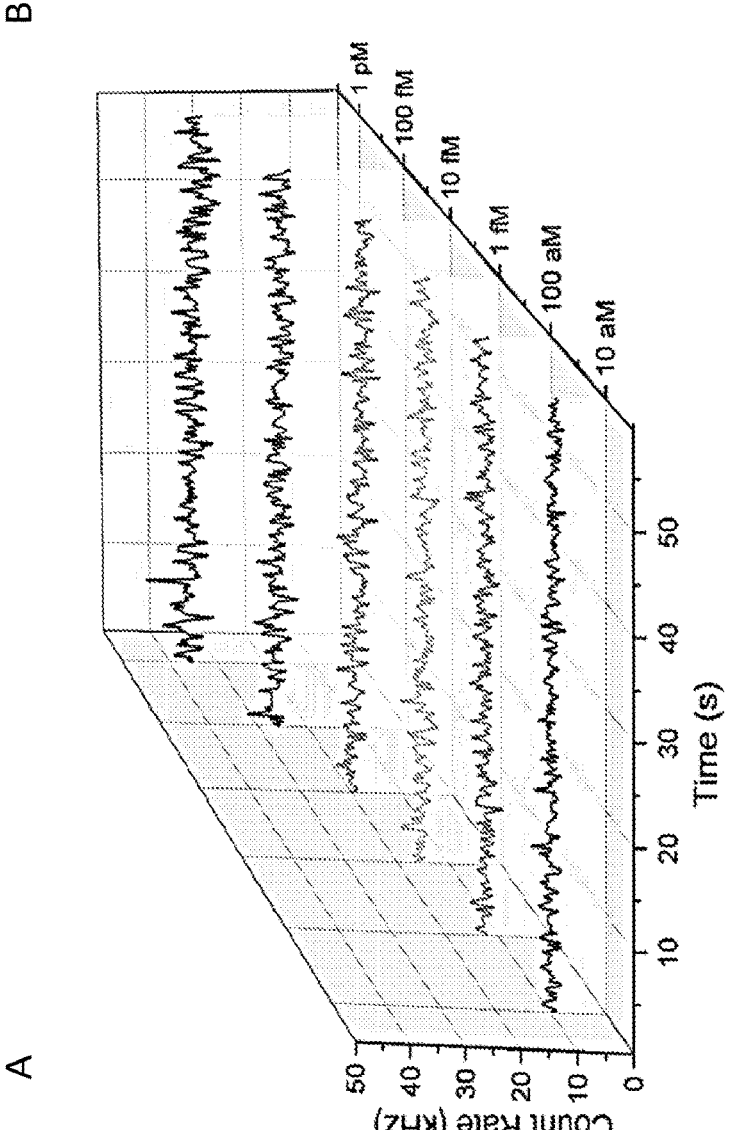
FIG. 7B depicts an exemplary histogram of average photon counts of serotype 3 DNA tetrahedron in the presence of different concentration of serotype 3 synthetic dengue viral RNA after 60 seconds.
Figure 8A:
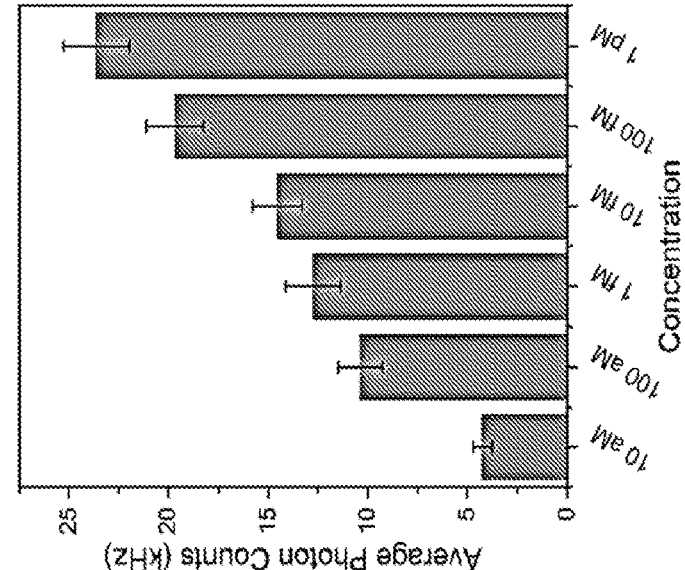
FIG. 8A depicts an exemplary photon count rate of the serotype 4 DNA tetrahedron in the presence of different concentrations of serotype 4 synthetic dengue viral RNA.
Figure 8B:
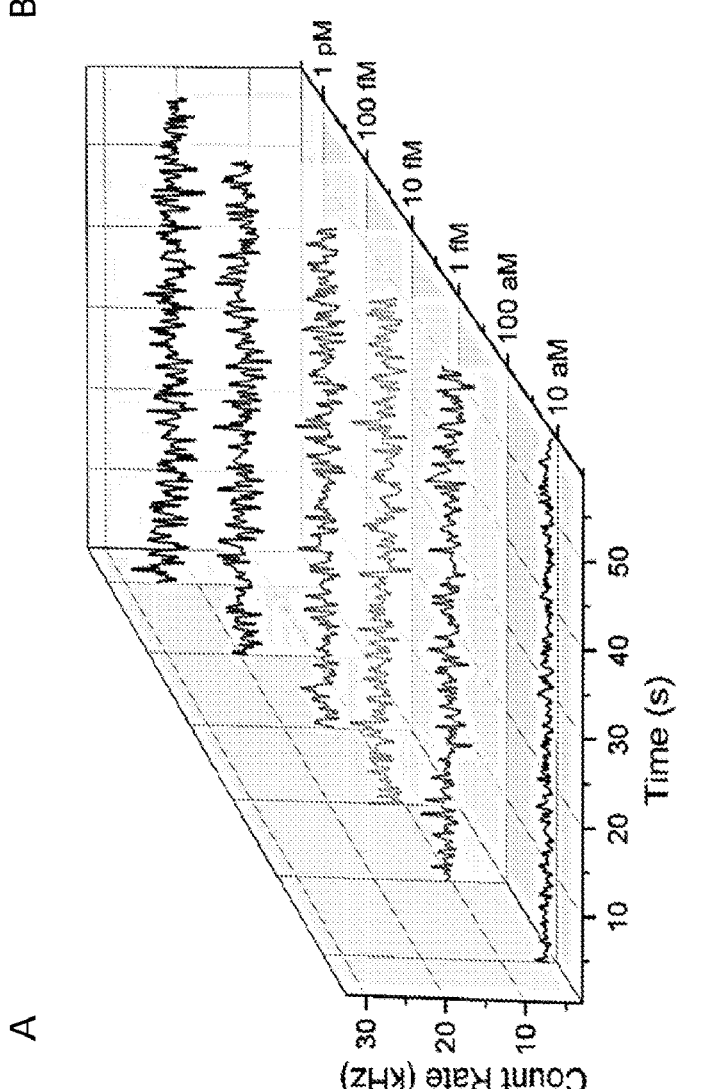
FIG. 8B depicts an exemplary histogram of average photon counts of serotype 4 DNA tetrahedron in the presence of different concentration of serotype 4 synthetic dengue viral RNA after 60 seconds.

The fluorescence recovery after the addition of corre-sponding synthesized target RNAs was visualized by fluo-rescence imaging (Azure Imaging System). The concentra-tion of RNA gradually increased from 10 pM to 10 nM, which resulted in a corresponding enhancement of fluores-cence intensity (FIG. 4A). The fluorescent intensities were extracted for each spot using an RGB color model. By reading out the intensities of green color of each of the pixels in the spot and determining their sum, the fluorescence intensity was quantified (FIG. 4B). To verify feasibility, a single molecule technique was used to detect the fluores-cence intensity after the addition of target RNA. The cor-responding photon count curves are presented in FIG. 5 through FIG. 8. In the presence of target RNA, the TET-labelled Protector DNA was released from the DNA tetra-hedron and its fluorescence intensity was restored as it separated spatially from the BHQ-1 quencher; this produced additional photons and was detected by the single molecule system. At extremely low concentration (10 aM~1 pM), the target RNA still triggered the tTMDRs in a concentration-dependent fashion.

Figures 9A, 9B, 9C, 9D:
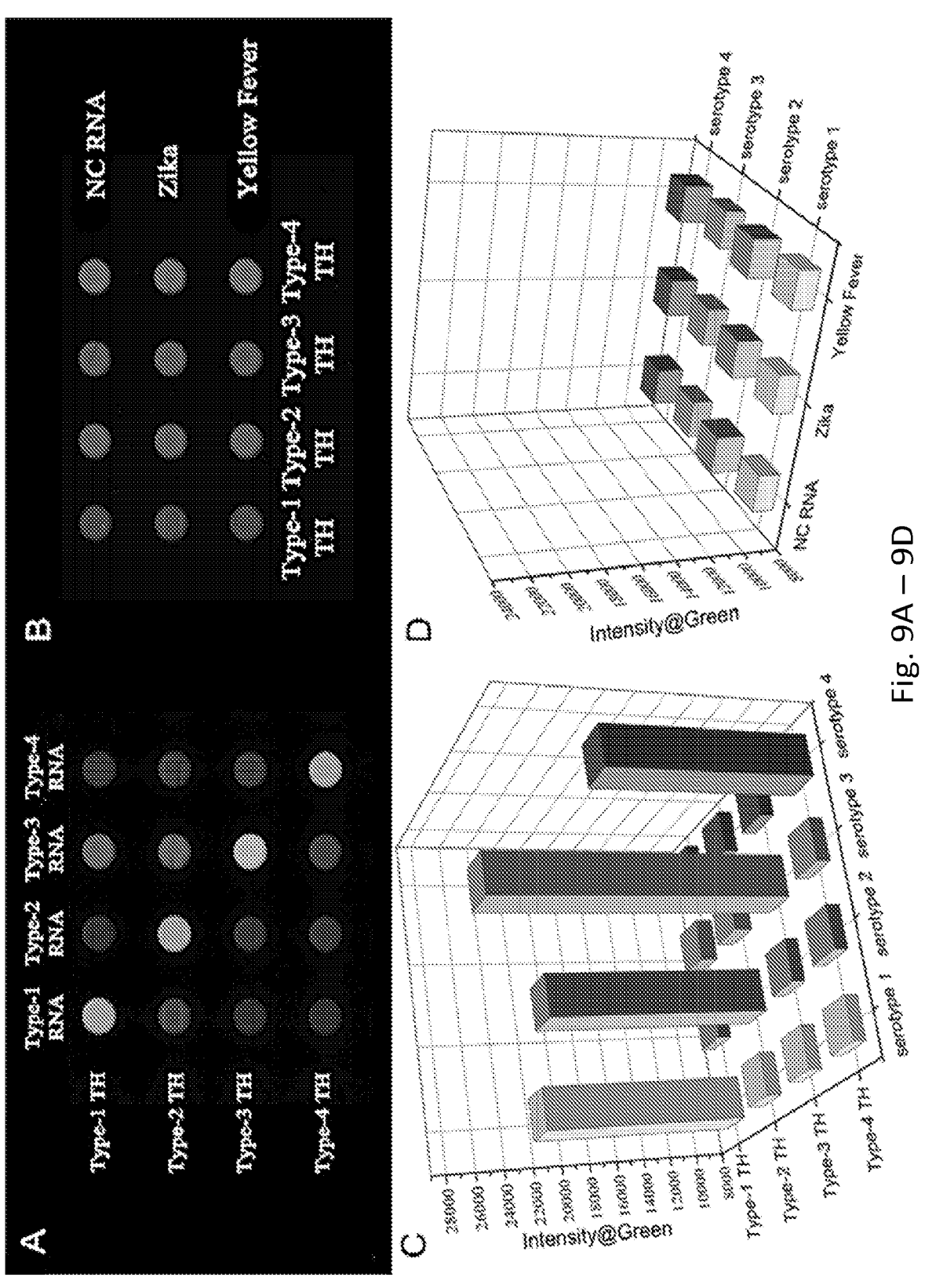
FIG. 9A through FIG. 9D depict exemplary experiments demonstrating the serotype specificity and exclusivity of the DENV tTMDRs.

The specificity of this system was evaluated using a fluorescence imager. For each DNA tetrahedron, one of the four different serotypes of RNA was added, respectively. As shown in FIG. 9A and FIG. 9C, DNA tetrahedrons produced intense fluorescence only in the presence of the correspond-ing DENV serotype RNA. No cross reactivity among the four serotypes was observed. The exclusivity was tested using an unmatched negative control RNA (NC RNA) sequence and extracted genomic RNA from Zika virus (strain PRVABC59) and yellow fever virus (Asibi strain). The negative control RNA was a synthetic RNA which was completely mismatched to all four tetrahedrons. As shown in FIG. 9B and FIG. 9D, none of the four DNA tetrahedrons produced incremental fluorescence in the presence of these RNA samples. These results indicated the reliability of this method of sequence detection.

Spiked Clinical Samples.

Figure 10A:
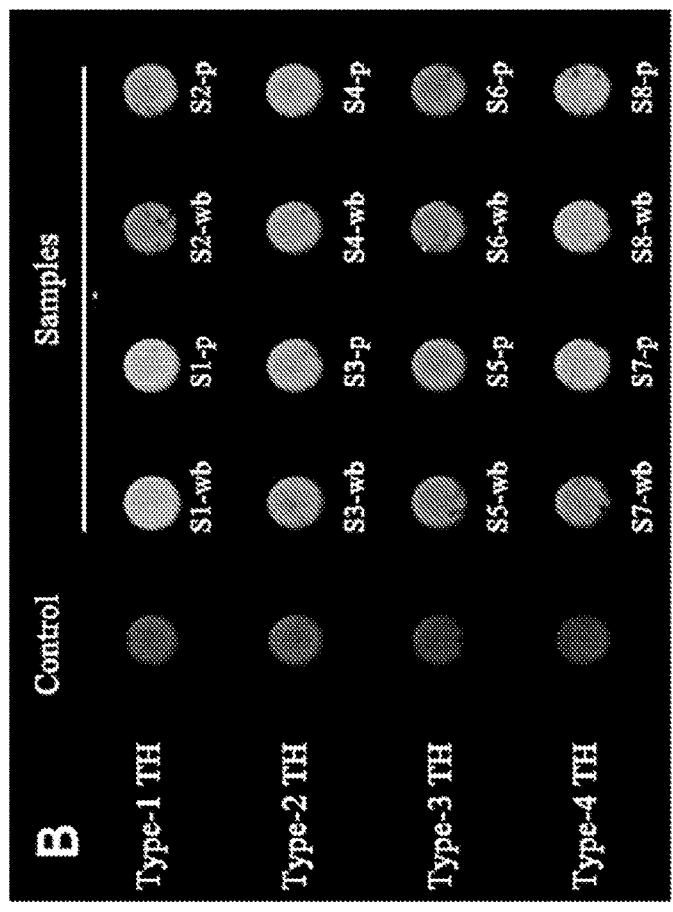
FIG. 10A and FIG. 10B depict exemplary experiments demonstrating detection of spiked clinical samples using the novel DENV tTMDRs.
Figure 10B:
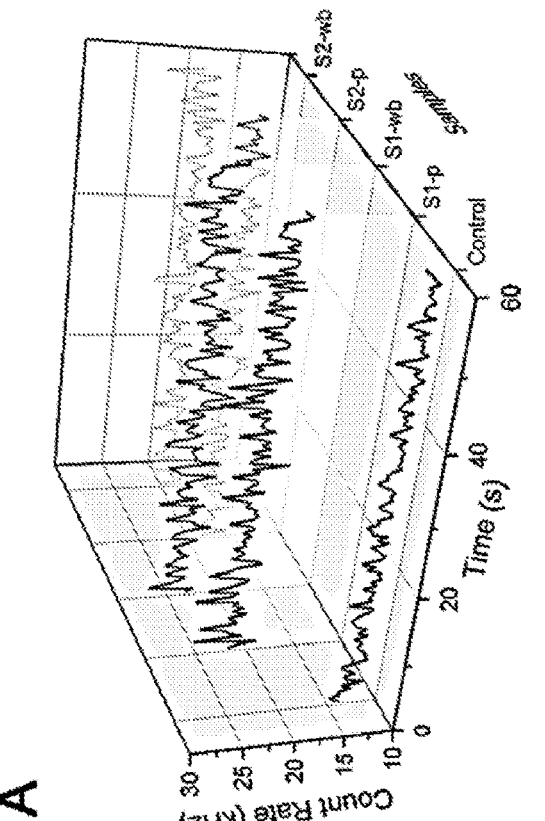
Figure 11:
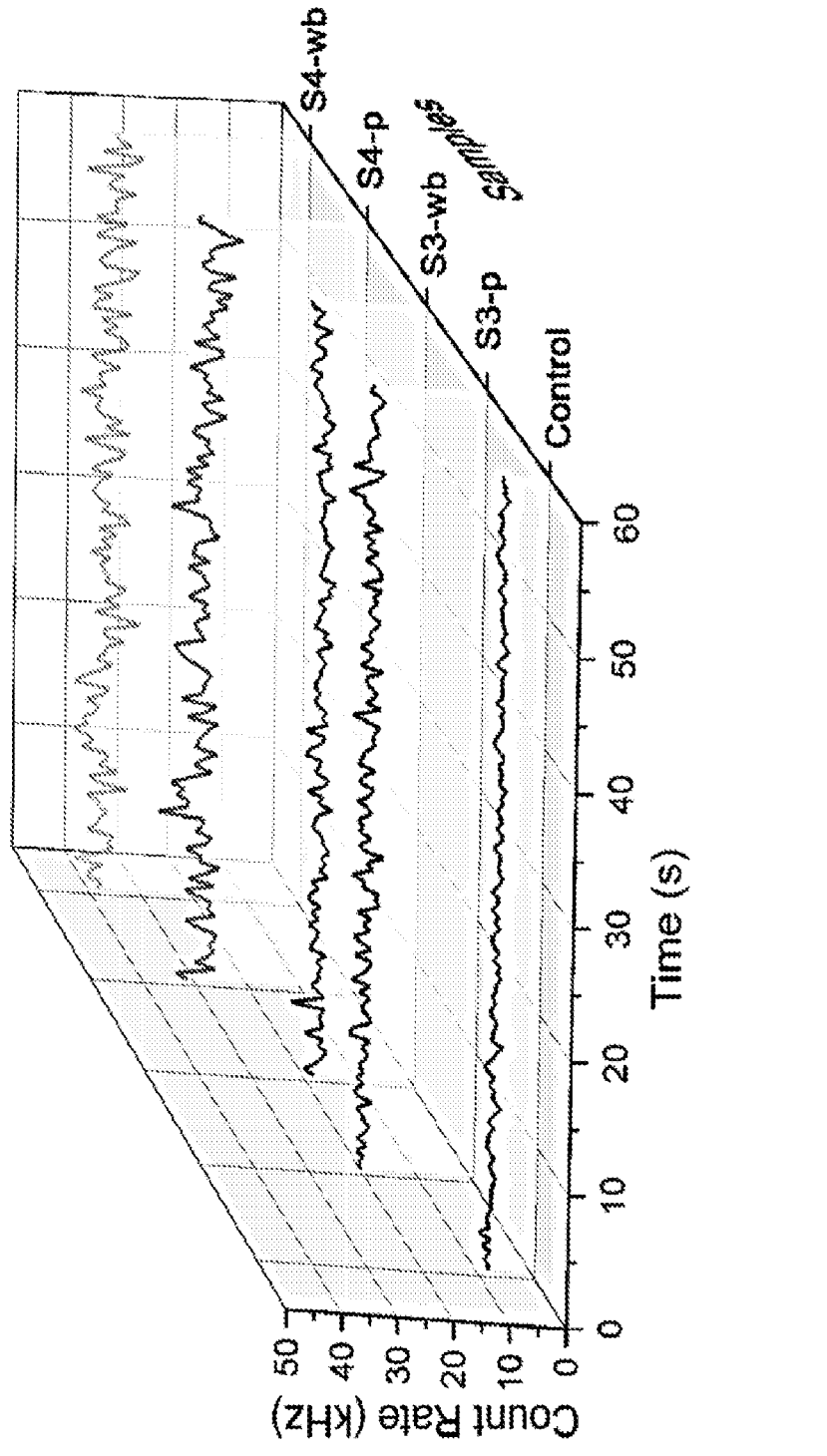
FIG. 11 depicts exemplary photon count rates of serotype 2 DNA tetrahedron in the presence clinical dengue viral RNA samples. S3 and S4 indicate the third and the forth patients, p indicates the sample was extracted from plasma, wb indicates the sample was extracted from whole blood.
Figure 12:
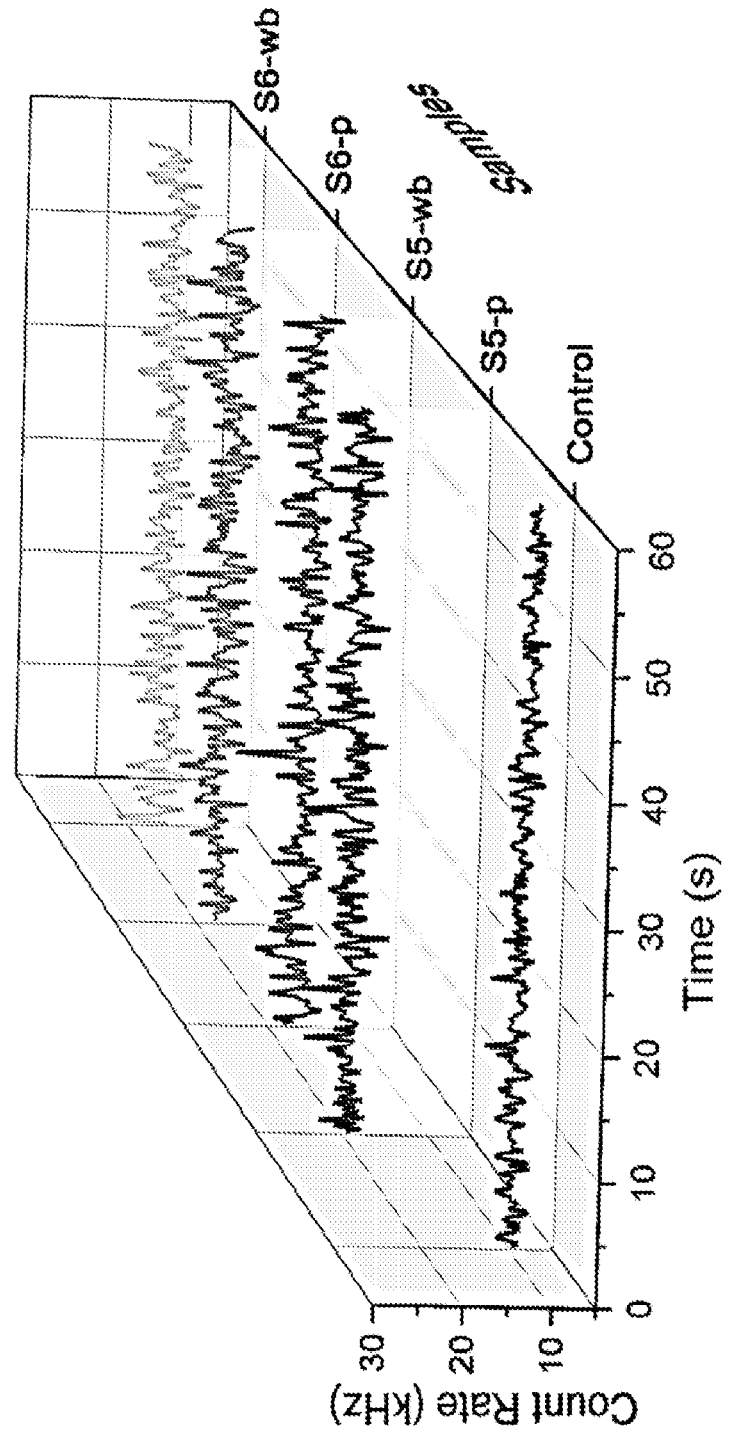
FIG. 12 depicts exemplary photon count rates of serotype 3 DNA tetrahedron in the presence clinical dengue viral RNA samples. S5 and S6 indicate the fifth and the sixth patients, p indicates the sample was extracted from plasma, wb indicates the sample was extracted from whole blood.
Figure 13:
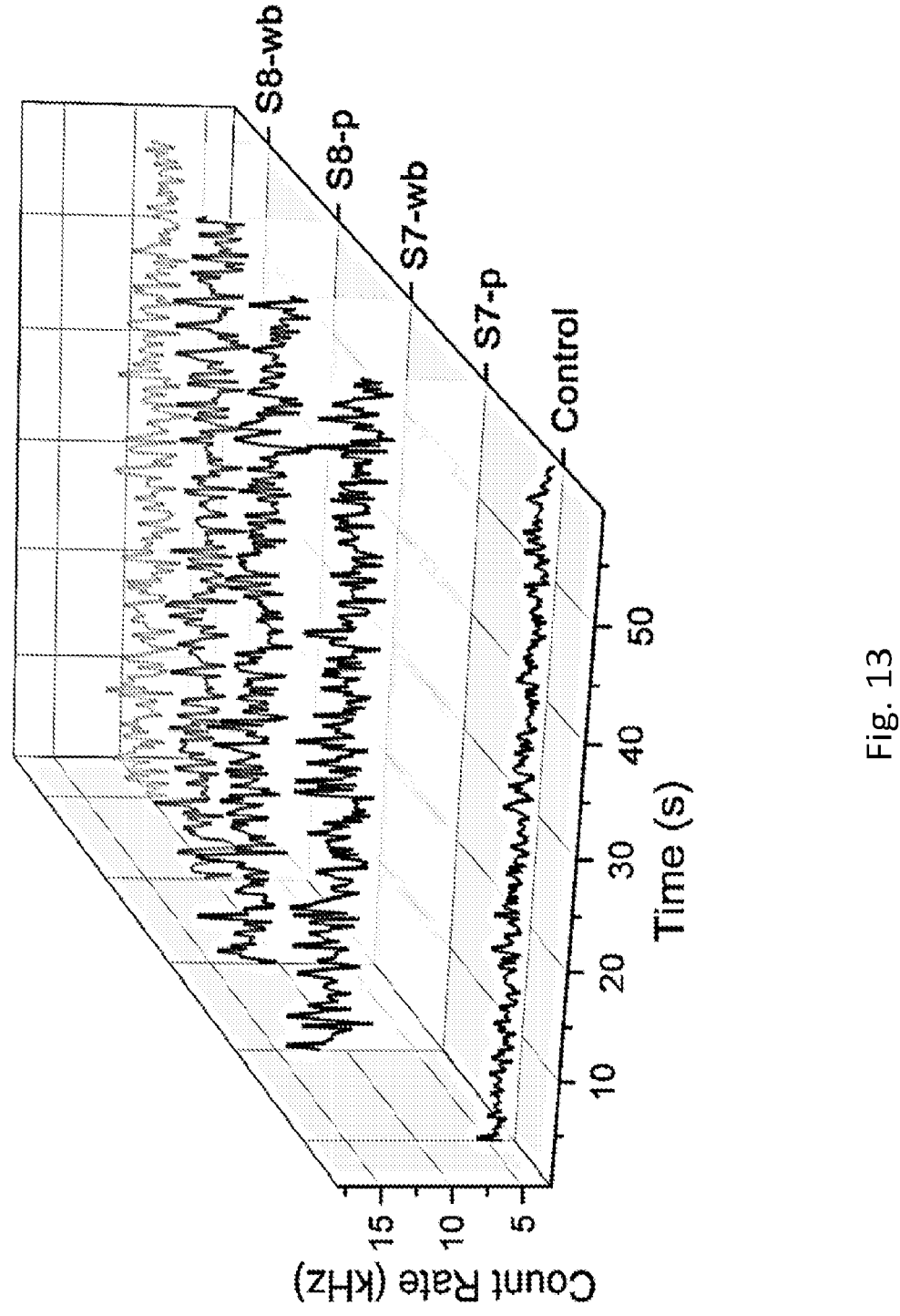
FIG. 13 depicts exemplary photon count rates of serotype 4 DNA tetrahedron in the presence clinical dengue viral RNA samples. S7 and S8 indicate the seventh and the eighth patients, p indicates the sample was extracted from plasma, wb indicates the sample was extracted from whole blood.

After confirming the feasibility and selectivity of the detection system, this novel strategy was used to detect DENV RNA from spiked clinical samples. DENV-negative whole blood and plasma samples were spiked with culture supernatant of each serotype to mimic concentrations observed in acute-phase clinical samples. After spiking, total nucleic acids were extracted and viral load was quantified using a laboratory-developed rRT-PCR (Waggoner et al., 2013, J Clin Microbiol, 51:3418-3420; Waggoner et al., 2013, PLoS Negl Trop Dis, 7: e2116). The higher concen-tration samples had an average concentration of 7.4 $\log_{10}$ copies/mL (SD 0.5; FIG. 10B, odd-numbered samples) and the lower concentration sample had an average concentra-tion of 5.6 $\log_{10}$ copies/mL (SD 0.6; FIG. 10B, even-numbered samples).

First, DENV detection from clinical samples was verified using the single molecule detection system. The photon counts increased after the addition of the RNAs (FIG. 10A, and FIG. 11 through FIG. 13). Then, a 384-well plate was used to prepare an array for diagnosis of the four serotypes of dengue RNA from these patient samples. After adding the clinical RNA samples to the corresponding tetrahedron solutions, and incubating at room temperature for 6 hours, the plate was scanned using an Azure Imaging System. All of the clinical samples gave the anticipated results (FIG. 14B). In addition, there was no significant difference between the samples derived from whole blood or plasma.

The disclosures of each and every patent, patent applica-tion, and publication cited herein are hereby incorporated herein by reference in their entirety. While this disclosure has been disclosed with reference to specific embodiments, it is apparent that other embodiments and variations of this disclosure may be devised by others skilled in the art without departing from the true spirit and scope of the disclosure. The appended claims are intended to be construed to include all such embodiments and equivalent variations.

What is claimed is:

1. A system for detecting a nucleic acid from a virus or viral subtype in a sample, the system comprising:
    at least four DNA-nanostructures, wherein each of the at least four DNA-nanostructures comprises a hybridization region specific for a nucleic acid molecule from a unique viral type or viral serotype selected from the group consisting of DENV1, DENV2, DENV3, and DENV4, wherein:
    the DNA-nanostructure specific for DENV1 is generated from hybridization of four oligonucleotides having at least about 95% sequence identity to SEQ ID NO:1, SEQ ID NO:5, SEQ ID NO:6 and SEQ ID NO:7,
    the DNA-nanostructure specific for DENV2 is generated from hybridization of four oligonucleotides having at least about 95% sequence identity to SEQ ID NO:2, SEQ ID NO:5, SEQ ID NO:6 and SEQ ID NO:7, the DNA-nanostructure specific for DENV3 is generated from hybridization of four oligonucleotides having at least about 95% sequence identity to SEQ ID NO:3, SEQ ID NO:5, SEQ ID NO:6 and SEQ ID NO:7, and the DNA-nanostructure specific for DENV4 is generated from hybridization of four oligonucleotides having at least about 95% sequence identity to SEQ ID NO:4, SEQ ID NO:5, SEQ ID NO:6 and SEQ ID NO:7, at least four protector oligonucleotides, wherein each of the at least four protector oligonucleotides is specific for hybridization to a unique DNA-nanostructure, and at least four capture oligonucleotides, wherein each of the at least four capture oligonucleotides is specific for hybridization to a unique DNA-nanostructure, wherein each of the at least four DNA-nanostructures is operably linked to one of a fluorophore or a quencher selected from a fluorophore quencher pair, wherein the quencher is capable of quenching the fluorescent light emitted from the fluorophore, and further wherein the protector oligonucleotide is operably linked to the other of a fluorophore and a quencher selected from the fluorophore quencher pair, wherein the viral nucleic acid is capable of displacing the protector oligonucleotide and hybridizing to the DNA-nanostructure; and wherein the capture oligonucleotide is capable of displacing the viral nucleic acid and hybridizing to the DNA-nanostructure but is not capable of displacing the protector oligonucleotide.

2. The system of claim 1, wherein the protector oligonucleotides comprise nucleic acid sequences having at least about 95% sequence identity to SEQ ID NO:8, SEQ ID NO:9, SEQ ID NO:10 and SEQ ID NO:11.

3. The system of claim 1, wherein the capture oligonucleotides comprise nucleic acid sequences having at least about 95% sequence identity to SEQ ID NO:12, SEQ ID NO:13, SEQ ID NO:14 and SEQ ID NO:15.

4. The system of claim 1, comprising a single composition comprising four DNA-nanostructures, wherein each of the at least four DNA-nanostructures or each of the at least four protector oligonucleotides are operably linked to unique fluorescent molecules.

5. The system of claim 4, wherein each of the at least four DNA nanostructure and protector oligonucleotides are operably linked to a fluorophore quencher pair selected from the group consisting of TET/BHQ1, FAM/BHQ1, TAMRA/BHQ2, JOE/BHQ1, ROX/BHQ2, HEX/BHQ1, NED/BHQ2, Cy3/BHQ2, Cy5/BHQ2, Cy5/BHQ3, and 6-FAM/BHQ1.

6. A kit comprising a system for detecting a nucleic acid from a virus or viral subtype in a sample, the kit comprising:

at least four DNA-nanostructures, wherein each of the at least four DNA-nanostructures comprises a hybridization region specific for a nucleic acid molecule from a unique viral type or viral serotype selected from the group consisting of DENV1, DENV2, DENV3, and DENV4, wherein:

the DNA-nanostructure specific for DENV1 is generated from hybridization of four oligonucleotides having at least about 95% sequence identity to SEQ ID NO:1, SEQ ID NO:5, SEQ ID NO:6 and SEQ ID NO:7, the DNA-nanostructure specific for DENV2 is generated from hybridization of four oligonucleotides having at least about 95% sequence identity to SEQ ID NO:2, SEQ ID NO:5, SEQ ID NO:6 and SEQ ID NO:7, the DNA-nanostructure specific for DENV3 is generated from hybridization of four oligonucleotides having at least about 95% sequence identity to SEQ ID NO:3, SEQ ID NO:5, SEQ ID NO:6 and SEQ ID NO:7, and the DNA-nanostructure specific for DENV4 is generated from hybridization of four oligonucleotides having at least about 95% sequence identity to SEQ ID NO:4, SEQ ID NO:5, SEQ ID NO:6 and SEQ ID NO:7, at least four protector oligonucleotides, wherein each of the at least four protector oligonucleotides is specific for hybridization to a unique DNA-nanostructure, and at least four capture oligonucleotides, wherein each of the at least four capture oligonucleotides is specific for hybridization to a unique DNA-nanostructure, wherein each of the at least four DNA-nanostructures is operably linked to one of a fluorophore or a quencher selected from a fluorophore quencher pair, wherein the quencher is capable of quenching the fluorescent light emitted from the fluorophore, and further wherein the protector oligonucleotide is operably linked to the other of a fluorophore and a quencher selected from the fluorophore quencher pair, wherein the viral nucleic acid is capable of displacing the protector oligonucleotide and hybridizing to the DNA-nanostructure; and wherein the capture oligonucleotide is capable of displacing the viral nucleic acid and hybridizing to the DNA-nanostructure but is not capable of displacing the protector oligonucleotide.

7. The kit of claim 6, wherein:

a) the protector oligonucleotides comprise nucleic acid sequences having at least about 95% sequence identity to SEQ ID NO:8, SEQ ID NO:9, SEQ ID NO: 10 and SEQ ID NO: 11; and b) associated the capture oligonucleotides comprise nucleic acid sequences having at least about 95% sequence identity to SEQ ID NO:12, SEQ ID NO:13, SEQ ID NO: 14 and SEQ ID NO:15.

8. A method of diagnosing a subject in need thereof as having an infection with a virus or viral serotype, the method comprising:

a) obtaining a sample from the subject;

b) contacting the sample from the subject with at least four DNA-nanostructures, wherein each DNA-nanostructure comprises a hybridization region specific for a unique viral type or viral serotype selected from the group consisting of DENV1, DENV2, DENV3, and DENV4, and further wherein each DNA-nanostructure is bound to a protector oligonucleotide, wherein:

the DNA-nanostructure specific for DENV1 is generated from hybridization of four oligonucleotides having at least about 95% sequence identity to SEQ ID NO:1, SEQ ID NO: 5, SEQ ID NO:6 and SEQ ID NO:7, the DNA-nanostructure specific for DENV2 is generated from hybridization of four oligonucleotides having at least about 95% sequence identity to SEQ ID NO:2, SEQ ID NO: 5, SEQ ID NO:6 and SEQ ID NO:7, the DNA-nanostructure specific for DENV3 is generated from hybridization of four oligonucleotides having at least about 95% sequence identity to SEQ ID NO:3, SEQ ID NO: 5, SEQ ID NO:6 and SEQ ID NO:7, and the DNA-nanostructure specific for DENV4 is generated from hybridization of four oligonucleotides having at least about 95% sequence identity to SEQ ID NO:4, SEQ ID NO: 5, SEQ ID NO:6 and SEQ ID NO:7;

wherein each of the at least four DNA-nanostructures is operably linked to one of a fluorophore or a quencher selected from a fluorophore quencher pair, wherein the quencher is capable of quenching the fluorescent light emitted from the fluorophore, and further wherein the protector oligonucleotide specific for hybridizing to the DNA-nanostructure is operably linked to the other of the fluorophore and a quencher selected from the fluorophore quencher pair; and wherein the viral nucleic acid is capable of displacing the protector oligonucleotide and hybridizing to the DNA-nanostructure;

c) contacting the reaction of step b) with at least four capture oligonucleotides, wherein each capture oligonucleotide is specific for hybridizing to one of the DNA-nanostructure and wherein the capture oligonucleotide is capable of displacing the viral nucleic acid and hybridizing to the DNA-nanostructure but is not capable of displacing the protector oligonucleotide, d) measuring fluorescence from the displaced protector oligonucleotide; and e) differentially diagnosing the subject as having a specific viral or viral serotype infection based on detection of fluorescence from a displaced protector oligonucleotide.

9. The method of claim 8, wherein the protector oligonucleotides comprise nucleic acid sequences having at least about 95% sequence identity to SEQ ID NO:8, SEQ ID NO:9, SEQ ID NO:10 and SEQ ID NO:11.

10. The method of claim 8, wherein the capture oligonucleotides comprise nucleic acid sequences having at least about 95% sequence identity to SEQ ID NO:12, SEQ ID NO:13, SEQ ID NO:14 and SEQ ID NO:15.

11. The method of claim 8, wherein the sample is aliquoted into at least four aliquots and contacted with each of the at least four DNA-nanostructures in parallel.

* * * * *

SEQUENCE LISTING

<160> NUMBER OF SEQ ID NOS: 24

<210> SEQ ID NO 1
<211> LENGTH: 71
<212> TYPE: DNA
<213> ORGANISM: Artificial Sequence
<220> FEATURE:
<223> OTHER INFORMATION: Chemically Synthesized, Type1 -DNA 1

<400> SEQUENCE: 1
tgctcttccc gaaaacagca tattgacgct ggcaactccc actcaactgc ctggtgatac    60
gaggatgggc a                                                         71

<210> SEQ ID NO 2
<211> LENGTH: 71
<212> TYPE: DNA
<213> ORGANISM: Artificial Sequence
<220> FEATURE:
<223> OTHER INFORMATION: Chemically Synthesized, Type2 -DNA 1

<400> SEQUENCE: 2
tgctcttccc gaaaacattt catgttagtt ttgccttctc actcaactgc ctggtgatac    60
gaggatgggc a                                                         71

<210> SEQ ID NO 3
<211> LENGTH: 71
<212> TYPE: DNA
<213> ORGANISM: Artificial Sequence
<220> FEATURE:
<223> OTHER INFORMATION: Chemically Synthesized, Type3 -DNA 1

<400> SEQUENCE: 3
tgctcttccc gaacatgatg acttcttctt ttaacgtcca actcaactgc ctggtgatac    60
gaggatgggc a                                                         71

<210> SEQ ID NO 4
<211> LENGTH: 71
<212> TYPE: DNA
<213> ORGANISM: Artificial Sequence
<220> FEATURE:
<223> OTHER INFORMATION: Chemically Synthesized, Type4 -DNA 1

<400> SEQUENCE: 4
tgctcttccc gaagacaacc aaatcctctc ttttccctac actcaactgc ctggtgatac    60
gaggatgggc a                                                         71

<210> SEQ ID NO 5
<211> LENGTH: 63
<212> TYPE: DNA
<213> ORGANISM: Artificial Sequence
<220> FEATURE:
<223> OTHER INFORMATION: Chemically Synthesized, DNA 2

<400> SEQUENCE: 5
ggtgataaaa cgtgtagcaa gctgtaatcg acgggaagag catgcccatc cactactatg    60
gcg                                                                  63

<210> SEQ ID NO 6
<211> LENGTH: 63
<212> TYPE: DNA
<213> ORGANISM: Artificial Sequence
<220> FEATURE:
<223> OTHER INFORMATION: Chemically Synthesized, DNA 3

-continued

```
<400> SEQUENCE: 6
aggcagttga gacgaacatt cctaagtctg aaatttatca cccgccatag tagacgtatc        60
acc                                                                     63

<210> SEQ ID NO 7
<211> LENGTH: 43
<212> TYPE: DNA
<213> ORGANISM: Artificial Sequence
<220> FEATURE:
<223> OTHER INFORMATION: Chemically Synthesized, DNA 4

<400> SEQUENCE: 7
tcgattacag cttgctacac gattcagact taggaatgtt cgt                         43

<210> SEQ ID NO 8
<211> LENGTH: 16
<212> TYPE: DNA
<213> ORGANISM: Artificial Sequence
<220> FEATURE:
<223> OTHER INFORMATION: Chemically Synthesized, Type 1 -Protector DNA

<400> SEQUENCE: 8
aggcaagaag tcacta                                                       16

<210> SEQ ID NO 9
<211> LENGTH: 16
<212> TYPE: DNA
<213> ORGANISM: Artificial Sequence
<220> FEATURE:
<223> OTHER INFORMATION: Chemically Synthesized, Type 2 -Protector DNA

<400> SEQUENCE: 9
aaaactaaca tgaaat                                                       16

<210> SEQ ID NO 10
<211> LENGTH: 16
<212> TYPE: DNA
<213> ORGANISM: Artificial Sequence
<220> FEATURE:
<223> OTHER INFORMATION: Chemically Synthesized, Type 3 -Protector DNA

<400> SEQUENCE: 10
aaaagaagaa gtcatc                                                       16

<210> SEQ ID NO 11
<211> LENGTH: 16
<212> TYPE: DNA
<213> ORGANISM: Artificial Sequence
<220> FEATURE:
<223> OTHER INFORMATION: Chemically Synthesized, Type 4 -Protector DNA

<400> SEQUENCE: 11
aagagaggat ttggtt                                                       16

<210> SEQ ID NO 12
<211> LENGTH: 23
<212> TYPE: DNA
<213> ORGANISM: Artificial Sequence
<220> FEATURE:
<223> OTHER INFORMATION: Chemically Synthesized, Type 1 - Capture DNA

<400> SEQUENCE: 12
aacaaggcaa gaagtcacta tca                                               23
```

```
<210> SEQ ID NO 13
<211> LENGTH: 23
<212> TYPE: DNA
<213> ORGANISM: Artificial Sequence
<220> FEATURE:
<223> OTHER INFORMATION: Chemically Synthesized, Type 2 - Capture DNA

<400> SEQUENCE: 13
aggcaaaact aacatgaaat gtt                                              23

<210> SEQ ID NO 14
<211> LENGTH: 23
<212> TYPE: DNA
<213> ORGANISM: Artificial Sequence
<220> FEATURE:
<223> OTHER INFORMATION: Chemically Synthesized, Type 3 - Capture DNA

<400> SEQUENCE: 14
acgttaaaag aagaagtcat cat                                              23

<210> SEQ ID NO 15
<211> LENGTH: 23
<212> TYPE: DNA
<213> ORGANISM: Artificial Sequence
<220> FEATURE:
<223> OTHER INFORMATION: Chemically Synthesized, Type 4 - Capture DNA

<400> SEQUENCE: 15
ggaaaagaga ggatttggtt gtc                                              23

<210> SEQ ID NO 16
<211> LENGTH: 26
<212> TYPE: RNA
<213> ORGANISM: Dengue virus

<400> SEQUENCE: 16
aaaucaaaca aggcaagaag ucaggc                                           26

<210> SEQ ID NO 17
<211> LENGTH: 26
<212> TYPE: RNA
<213> ORGANISM: Dengue virus

<400> SEQUENCE: 17
gguagaaggc aaaacuaaca ugaaac                                           26

<210> SEQ ID NO 18
<211> LENGTH: 26
<212> TYPE: RNA
<213> ORGANISM: Dengue virus

<400> SEQUENCE: 18
caaggacguu aaaagaagaa gucagg                                           26

<210> SEQ ID NO 19
<211> LENGTH: 26
<212> TYPE: RNA
<213> ORGANISM: Dengue virus

<400> SEQUENCE: 19
accuagggaa aagagaggau uugugg                                           26

<210> SEQ ID NO 20
<211> LENGTH: 71
```

```
<212> TYPE: DNA
<213> ORGANISM: Artificial Sequence
<220> FEATURE:
<223> OTHER INFORMATION: Chemically Synthesized, DNA tetrahedron strand
      with a variable hybridization region
<220> FEATURE:
<221> NAME/KEY: misc_feature
<222> LOCATION: (13)..(40)
<223> OTHER INFORMATION: any nucleotide

<400> SEQUENCE: 20
tgctcttccc gannnnnnnn nnnnnnnnnn nnnnnnnnnn actcaactgc ctggtgatac      60
gaggatgggc a                                                          71

<210> SEQ ID NO 21
<211> LENGTH: 28
<212> TYPE: DNA
<213> ORGANISM: Artificial Sequence
<220> FEATURE:
<223> OTHER INFORMATION: Chemically Synthesized, hybridization sequence
      for tye 1

<400> SEQUENCE: 21
aaacagcata ttgacgctgg caactccc                                        28

<210> SEQ ID NO 22
<211> LENGTH: 28
<212> TYPE: DNA
<213> ORGANISM: Artificial Sequence
<220> FEATURE:
<223> OTHER INFORMATION: Chemically Synthesized, hybridization sequence
      for tye 2

<400> SEQUENCE: 22
aaacatttca tgttagtttt gccttctc                                        28

<210> SEQ ID NO 23
<211> LENGTH: 28
<212> TYPE: DNA
<213> ORGANISM: Artificial Sequence
<220> FEATURE:
<223> OTHER INFORMATION: Chemically Synthesized, hybridization sequence
      for tye 3

<400> SEQUENCE: 23
acatgatgac ttcttctttt aacgtcca                                        28

<210> SEQ ID NO 24
<211> LENGTH: 28
<212> TYPE: DNA
<213> ORGANISM: Artificial Sequence
<220> FEATURE:
<223> OTHER INFORMATION: Chemically Synthesized, hybridization sequence
      for tye 4

<400> SEQUENCE: 24
agacaaccaa atcctctctt ttccctac                                        28
```